(12) United States Patent
Thirugnanasambandam et al.

(10) Patent No.: US 9,668,882 B2
(45) Date of Patent: Jun. 6, 2017

(54) BIOMEDICAL IMPLANT INSERTERS AND RELATED APPARATUS, SYSTEMS, AND METHODS

(71) Applicant: Amedica Corporation, Salt Lake City, UT (US)

(72) Inventors: Prabhakar Thirugnanasambandam, Midvale, UT (US); John Cobb, Lafayette, LA (US); William Atkinson, Lafayette, LA (US); Peter Harris, Boca Raton, FL (US); Chad Wayne Lewis, Layton, UT (US)

(73) Assignee: Amedica Corporation, Salt Lake City, UT (US)

( * ) Notice: Subject to any disclaimer, the term of this patent is extended or adjusted under 35 U.S.C. 154(b) by 481 days.

(21) Appl. No.: 14/175,902

(22) Filed: Feb. 7, 2014

(65) Prior Publication Data

US 2014/0172107 A1     Jun. 19, 2014

Related U.S. Application Data

(63) Continuation-in-part of application No. 12/896,292, filed on Oct. 1, 2010, now Pat. No. 8,821,578, and application No. 14/175,902, Feb. 7, 2014.

(Continued)

(51) Int. Cl.
*A61F 2/46* (2006.01)
*A61F 2/44* (2006.01)
*A61F 2/30* (2006.01)

(52) U.S. Cl.
CPC .......... *A61F 2/4611* (2013.01); *A61F 2/442* (2013.01); *A61F 2/4465* (2013.01);
(Continued)

(58) Field of Classification Search
CPC ..................................................... A61F 2/4611
(Continued)

(56) References Cited

U.S. PATENT DOCUMENTS

| 5,683,463 | A  | * | 11/1997 | Godefroy | ............... | A61F 2/446 |
| | | | | | | 623/17.16 |
| 6,436,139 | B1 | * | 8/2002 | Shapiro | .................. | A61F 2/446 |
| | | | | | | 623/17.11 |

(Continued)

OTHER PUBLICATIONS

International Search Report for PCT/US14/15411, Apr. 30, 2014, 2 pgs.
(Continued)

*Primary Examiner* — David Bates
(74) *Attorney, Agent, or Firm* — Polsinelli PC

(57) ABSTRACT

Embodiments of apparatus, systems, and methods relating to spinal implants. In some embodiments, the spinal implant may comprise a first sidewall, a second sidewall opposite from the first sidewall, a pair of opposed frictional surfaces each comprising a plurality of raised structures, a first end wall joining the pair of opposed sidewall surfaces, and a second end wall joining the first sidewall and the second sidewall. The second end wall may comprise a recess formed by a first wall portion and a second wall portion arranged at an angle to one another to form a fish-tailed structure configured to be engaged with an inserter instrument. The interface between the recess and the inserter instrument may be configured to at least substantially eliminate any point or line contacts between the inserter instrument and the spinal implant during a flip maneuver of the spinal implant within an intervertebral space of a patient.

16 Claims, 25 Drawing Sheets

Related U.S. Application Data

(60) Provisional application No. 61/248,052, filed on Oct. 2, 2009, provisional application No. 61/762,135, filed on Feb. 7, 2013.

(52) U.S. Cl.
CPC ............... *A61F 2002/3082* (2013.01); *A61F 2002/30281* (2013.01); *A61F 2002/30779* (2013.01); *A61F 2002/30785* (2013.01); *A61F 2002/30843* (2013.01); *A61F 2002/30845* (2013.01); *A61F 2002/30878* (2013.01); *A61F 2002/30892* (2013.01); *A61F 2002/30904* (2013.01); *A61F 2002/4475* (2013.01); *A61F 2002/4629* (2013.01)

(58) Field of Classification Search
USPC .......................................... 623/17.11–17.16
See application file for complete search history.

(56) References Cited

U.S. PATENT DOCUMENTS

| | | | | |
|---|---|---|---|---|
| 6,503,279 | B1* | 1/2003 | Webb | A61F 2/4465 623/17.16 |
| 6,974,480 | B2 | 12/2005 | Messerli et al. | |
| 7,815,682 | B1 | 10/2010 | Peterson et al. | |
| 7,892,239 | B2 | 2/2011 | Warnick et al. | |
| 8,070,754 | B2* | 12/2011 | Fabian | A61B 17/025 606/86 A |
| 8,303,601 | B2* | 11/2012 | Bandeira | A61B 17/025 606/90 |
| 8,603,175 | B2* | 12/2013 | Thibodeau | A61F 2/4465 623/17.16 |
| 8,636,804 | B2* | 1/2014 | Errico | A61F 2/442 606/86 A |
| 8,840,620 | B2* | 9/2014 | Recoules-Arche | A61F 2/4465 606/99 |
| 9,044,337 | B2* | 6/2015 | Dinville | A61F 2/447 |
| 9,339,395 | B2* | 5/2016 | Prado | A61F 2/4601 |
| 9,345,586 | B2* | 5/2016 | Hunt | A61B 17/1671 |
| 2002/0045904 | A1* | 4/2002 | Fuss | A61B 17/02 606/99 |
| 2002/0045943 | A1* | 4/2002 | Uk | A61F 2/446 623/17.16 |
| 2002/0068973 | A1* | 6/2002 | Jackson | A61F 2/446 623/17.11 |
| 2002/0082695 | A1* | 6/2002 | Neumann | A61F 2/44 623/17.11 |
| 2003/0004576 | A1* | 1/2003 | Thalgott | A61F 2/4455 623/17.16 |
| 2003/0009222 | A1* | 1/2003 | Fruh | A61F 2/446 623/17.11 |
| 2003/0109928 | A1* | 6/2003 | Pasquet | A61F 2/4455 623/17.11 |
| 2003/0114931 | A1* | 6/2003 | Lee | A61F 2/4455 623/17.11 |
| 2003/0225414 | A1* | 12/2003 | Shimp | A61F 2/4611 606/99 |
| 2005/0049587 | A1* | 3/2005 | Jackson | A61F 2/446 623/17.11 |
| 2005/0071005 | A1* | 3/2005 | Carli | A61F 2/4455 623/17.11 |
| 2005/0177238 | A1* | 8/2005 | Khandkar | A61F 2/30767 623/17.11 |
| 2006/0030860 | A1* | 2/2006 | Peterman | A61F 2/4425 606/99 |
| 2006/0084986 | A1* | 4/2006 | Grinberg | A61B 17/025 606/86 A |
| 2006/0111784 | A1* | 5/2006 | Grinberg | A61F 2/0095 623/17.15 |
| 2006/0247679 | A1* | 11/2006 | Peterman | A61B 17/2812 606/207 |
| 2006/0247774 | A1* | 11/2006 | Gil | A61B 17/80 623/17.11 |
| 2007/0213826 | A1* | 9/2007 | Smith | A61F 2/4465 623/17.11 |
| 2007/0225726 | A1 | 9/2007 | Dye et al. | |
| 2007/0282441 | A1 | 12/2007 | Stream et al. | |
| 2008/0065082 | A1 | 3/2008 | Chang et al. | |
| 2008/0065219 | A1 | 3/2008 | Dye | |
| 2008/0071279 | A1* | 3/2008 | Bandeira | A61B 17/025 606/90 |
| 2008/0221694 | A1 | 9/2008 | Warnick et al. | |
| 2011/0230968 | A1* | 9/2011 | Perisic | A61F 2/447 623/17.16 |
| 2011/0245923 | A1 | 10/2011 | Cobb et al. | |
| 2012/0330420 | A1 | 12/2012 | Brodke et al. | |

OTHER PUBLICATIONS

Written Opinion for PCT/US14/15411, Apr. 30, 2014, 7 pgs.
European Search Report, Application No. 14749509.7, Jul. 8, 2016, 7 pgs.

\* cited by examiner

BIOMEDICAL IMPLANT INSERTERS AND RELATED APPARATUS, SYSTEMS, AND METHODS

RELATED APPLICATIONS

This application is a continuation-in-part of co-pending U.S. patent application Ser. No. 12/896,292 filed on Oct. 1, 2010 and titled "INTERVERTEBRAL IMPLANT DEVICE FOR A POSTERIOR INTERBODY FUSION SURGICAL PROCEDURE," which application claims the benefit of priority of U.S. Provisional Patent Application No. 61/248,052, filed on Oct. 2, 2009, and also titled "INTERVERTEBRAL IMPLANT DEVICE FOR A POSTERIOR INTERBODY FUSION SURGICAL PROCEDURE." This application also claims the benefit under 35 U.S.C. §119(e) of U.S. Provisional Patent Application No. 61/762,135 filed Feb. 7, 2013 and titled "SPINAL IMPLANT INSERTER AND RELATED APPARATUS AND METHODS." Each of the aforementioned applications is hereby incorporated herein by reference in its entirety.

SUMMARY

Disclosed herein are embodiments of apparatus, methods, and systems relating to spinal implants and other biomedical implants. In various exemplary embodiments, an intervertebral implant device may be provided for a posterior, anterior, lateral, or oblique interbody fusion surgical procedure. Advantageously, some embodiments may be configured such that the device may be surgically implanted in the spine of a patient through a minimal access window, thereby sparing and preserving the associated facets to the greatest degree possible.

In one exemplary embodiment, an intervertebral implant device may comprise: a pair of substantially parallel opposed arcuate surfaces; a pair of substantially parallel opposed surfaces each of which may comprise a plurality of raised structures; a substantially curved end wall joining the pair of parallel opposed arcuate surfaces; and a substantially recessed end wall joining the pair of parallel opposed arcuate surfaces; wherein the intervertebral implant device defines one or more voids in which a bone graft material is selectively disposed. The substantially recessed end wall may be configured to selectively and pivotably receive one or more surgical implantation devices. The substantially curved end wall may comprise one or more smoothed edges. The substantially recessed end wall may comprise a first wall portion and a second wall portion arranged at an angle to one another and collectively forming a fish-tailed structure. The recessed feature may be concave or convex, or may otherwise comprise only or more concave or convex portions.

The substantially recessed end wall may comprise one or more of a hole and a recess configured to selectively receive a surgical tool. The one or more voids defined by the intervertebral implant device may pass through one or more of the pair of substantially parallel opposed arcuate surfaces and the pair of substantially parallel opposed frictional surfaces. The intervertebral implant device may be configured to be selectively disposed in an intervertebral space through an access window formed through bony and/or soft tissue structures.

In another exemplary embodiment, a surgical method for implanting an intervertebral implant device may comprise: providing an intervertebral implant device comprising: a pair of substantially parallel opposed arcuate surfaces; a pair of substantially parallel opposed frictional surfaces each comprising a plurality of raised structures; a substantially curved end wall joining the pair of parallel opposed arcuate surfaces; and a substantially recessed end wall joining the pair of parallel opposed arcuate surfaces; wherein the intervertebral implant device defines one or more voids in which a bone graft material is selectively disposed; and disposing the intervertebral implant device within an intervertebral space through an access window formed adjacent to a facet joint of a spine of a patient. The substantially recessed end wall may be configured to selectively and pivotably receive one or more surgical implantation devices. The substantially curved end wall may comprise one or more smoothed edges. The substantially recessed end wall may comprise a first wall portion and a second wall portion arranged at an angle to one another and collectively forming a fish-tailed structure. The substantially recessed end wall may comprise one or more of a hole and a recess configured to selectively receive a surgical tool. The one or more voids defined by the intervertebral implant device may pass through one or more of the pair of substantially parallel opposed arcuate surfaces and the pair of substantially parallel opposed frictional surfaces. The intervertebral implant device may be configured to be selectively disposed in an intervertebral space through the access window formed through bony and soft tissue structures to either the left or right of a centerline of a spine.

In a further exemplary embodiment, a surgical method for implanting an intervertebral implant device may comprise: forming an access window through bony and soft tissue structures to either the left or right of a centerline of a spine; passing bone graft material through the access window and into an adjacent intervertebral space; disposing bone graft material in an intervertebral implant device; passing the intervertebral implant device through the access window and into the adjacent intervertebral space; and positioning the intervertebral implant device within the intervertebral space. The intervertebral implant device may comprise: a pair of substantially parallel opposed arcuate surfaces; a pair of substantially parallel opposed frictional surfaces each including a plurality of raised structures; a substantially curved end wall joining the pair of parallel opposed arcuate surfaces; and a substantially recessed end wall joining the pair of parallel opposed arcuate surfaces. The intervertebral implant device may define one or more voids in which the bone graft material may be selectively disposed.

In one particular example of a system for installing a spinal implant, the system may comprise a spinal implant comprising: an upper surface; a lower surface; a first side wall surface; a second side wall surface opposite from the first side wall surface; a front end wall surface; and a rear end wall surface opposite from the front end wall surface. The rear end wall surface may comprise at least one of a recess and a protrusion comprising two at least substantially flat surfaces interconnected by a curved surface. The two at least substantially flat surfaces may be configured such that they are not parallel and extend relative to one another at a first angle. In other embodiments, the two surfaces interconnecting the curved surfaces may be curved. For example, some embodiments may comprise a sinusoidal interface.

The system may further comprise a tool, such as an inserter instrument, an intermediary piece, or an inserter instrument coupled with an intermediary piece, comprising at least one of a recess and a protrusion configured to fit within the corresponding recess or protrusion of the spinal implant. The at least one of a recess and a protrusion of the tool may comprise two at least substantially flat surfaces interconnected by a curved surface. As previously mentioned, the recess or protrusion may comprise one or more convex or concave portions configured to match a corresponding interface surface of the implant. The two at least substantially flat surfaces of the at least one of a recess and a protrusion of the tool may be configured such that they are not parallel and extend relative to one another at a second angle at least substantially identical to the first angle. The at least one of a recess and a protrusion of the tool may be further configured such that the curved surface of the at least one of a recess and a protrusion of the tool is configured to at least substantially mate and fit within the at least one of a recess and a protrusion of the spinal implant.

In some embodiments, the rear end wall surface may further comprise an opening configured to facilitate engagement with the tool.

In some embodiments, the first angle is at least about 90 degrees. In some such embodiments, the first angle is between about 90 degrees and about 120 degrees. In some such embodiments, the first angle is between about 100 degrees and about 110 degrees.

In some embodiments, the tool may comprise an inserter tool. The at least one of a recess and a protrusion of the inserter tool may be positioned at a distal end of the inserter tool.

In some embodiments, the tool may comprise an intermediary piece configured to be coupled with the spinal implant and a separate inserter tool in between the spinal implant and the inserter tool. In some embodiments, the intermediary piece may comprise a central opening extending all of the way through the intermediary piece. The central opening may be configured to receive a shaft, which shaft may be coupled with the inserter tool.

In some embodiments comprising an intermediary piece, the intermediary piece may comprise a first protrusion extending from a first end of the intermediary piece. The first protrusion may be configured to be received within a corresponding recess formed within the spinal implant. The intermediary piece may further comprise a second protrusion extending from a second end of the intermediary piece opposite from the first end. The second protrusion may be configured to be received within a corresponding recess formed within an inserter tool. In some embodiments, the second protrusion may extend along a plane that is at least substantially perpendicular to a plane along which the first protrusion extends. This may facilitate a more secure engagement between the spinal implant, the intermediary piece, and the inserter instrument. In some embodiments, the second protrusion may expand in diameter as the second protrusion extends away from a body of the intermediary piece.

The at least one of a recess and a protrusion of the spinal implant and the at least one of a recess and a protrusion of the tool may be configured such that the interface between the at least one of a recess and a protrusion of the spinal implant and the at least one of a recess and a protrusion of the tool at least substantially eliminates any point or line contacts between the tool and the spinal implant during a flip maneuver of the spinal implant within an intervertebral space of a patient. This may be particularly useful in connection with embodiments in which the spinal implant comprises a ceramic material, such as a silicon nitride ceramic material.

In another particular example of a system for installing a spinal implant, the system may comprise a spinal implant comprising: an upper surface; a lower surface; a first side wall surface; a second side wall surface opposite from the first side wall surface; a front end wall surface; and a rear end wall surface opposite from the front end wall surface. The rear end wall surface may comprise a recess comprising two at least substantially flat surfaces interconnected by a curved surface. The two at least substantially flat surfaces may be specifically configured such that they are not parallel and extend relative to one another at a first angle, which first angle may be between about 100 degrees and about 110 degrees. The rear end wall surface may further comprise an opening formed within the recess and configured to facilitate engagement with an inserter tool.

The inserter tool may comprise a protrusion configured to fit within the recess of the spinal implant. The protrusion may comprise two at least substantially flat surfaces interconnected by a curved surface. The two at least substantially flat surfaces of the protrusion may be configured such that they are not parallel and extend relative to one another at a second angle at least substantially identical to the first angle. The protrusion may be further configured such that the curved surface of the protrusion is configured to at least substantially mate and fit within the recess the spinal implant so as to at least substantially eliminate any point or line contacts between the inserter tool and the spinal implant during a flip maneuver of the spinal implant within an intervertebral space of a patient using the inserter tool.

In some embodiments, the inserter tool may further comprise an intermediary piece. In some such embodiments, the protrusion may be formed at a distal end of the intermediary piece.

In a particular example of an embodiment of a spinal implant, the implant may comprise: a first sidewall; a second sidewall opposite from the first sidewall; a pair of opposed frictional surfaces each comprising a plurality of raised structures; a first end wall joining the pair of opposed sidewall surfaces; and a second end wall joining the first sidewall and the second sidewall. The second end wall may comprise a recess formed by a first wall portion and a second wall portion arranged at an angle to one another to form a fish-tailed structure. The fish-tailed structure may be formed such that the first wall portion and the second wall portion extend from one another at an angle greater than ninety degrees. The fish-tailed structure may be formed so as to extend at least substantially all of the way along at least one dimension of the second end wall.

In some embodiments, the first wall portion may extend from and join with the first sidewall, and wherein the second wall portion may extend from and join with the second sidewall so as to form the fish-tailed structure.

In some embodiments, the central portion of the fish-tailed structure may be positioned to extend along an axis running along a mid point, or at least substantially a mid point, between the upper and lower surfaces (or opposed frictional surfaces). In other embodiments, the central portion of the fish-tailed structure may be positioned to extend along an axis running along a mid point, or at least substantially a midpoint, between the two opposing sidewalls of the implant. In some embodiments, the fish-tailed structure may further comprise a curved surface interconnecting the first wall portion and the second wall portion. In some such embodiments, the curved surface may comprise the central portion referenced above. In other embodiments, the central portion of the fish-tailed structure may be offset from the centerline or midpoint of the implant.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
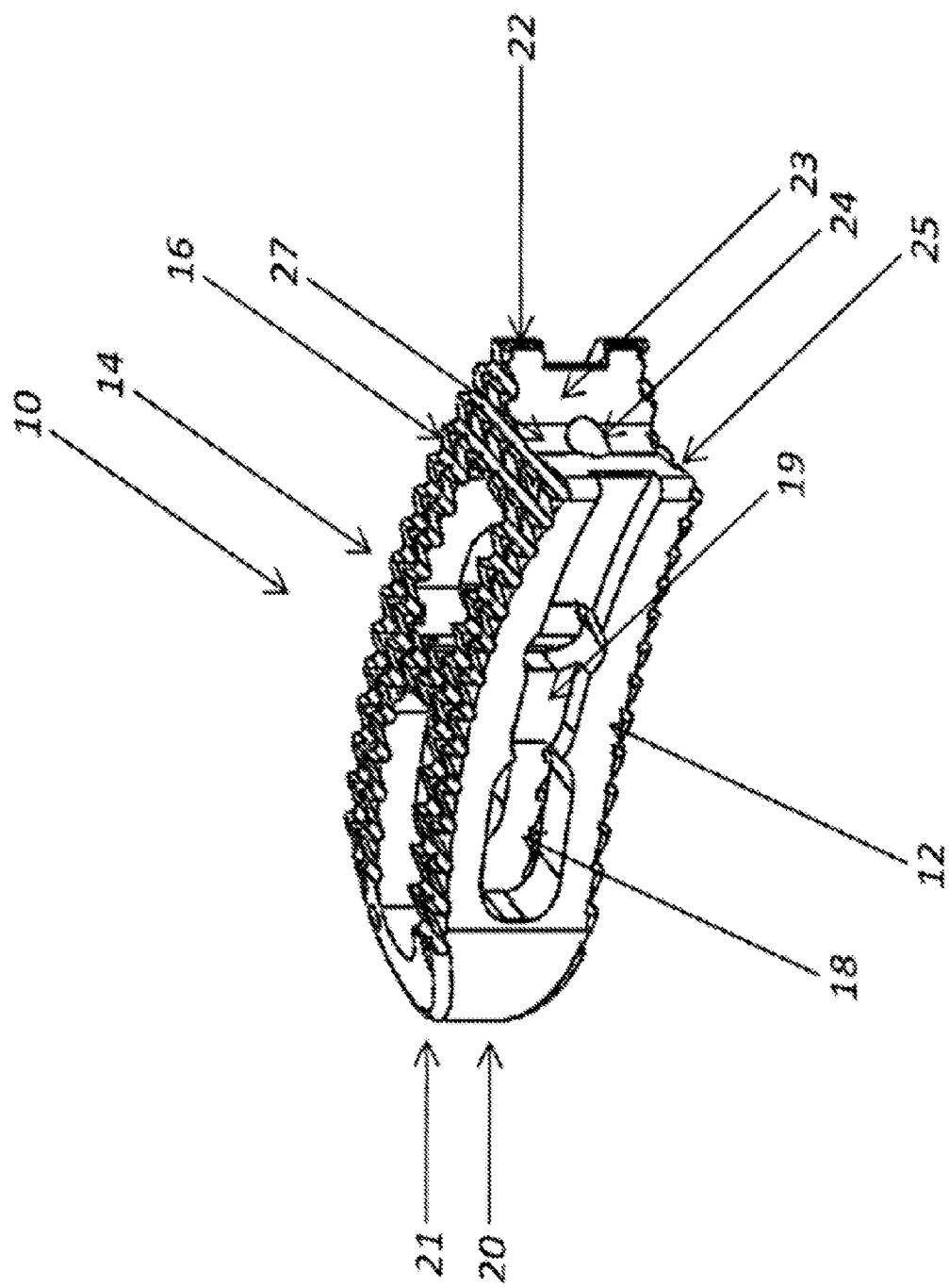
FIG. 1 is a perspective diagram illustrating one exemplary embodiment of an intervertebral implant device.

It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Various embodiments of apparatus, methods, and systems are disclosed herein that relate to spinal implants and instruments for installing biomedical implants. For example, some embodiments may comprise intervertebral spinal spacers. Some embodiments may comprise instruments for installing such intervertebral spinal implants and/or intermediary pieces configured for being positioned between an inserter and a spinal implant. In some embodiments, an intervertebral implant device for a posterior interbody fusion surgical procedure may be provided. In some such embodiments, this intervertebral implant device may be configured such that it may be surgically implanted in the spine of a patient through a minimal access window, thereby sparing and preserving the associated facets to the greatest degree possible.

In some embodiments, the interface between the implant and the instrument (the "inserter") for installing the implant may be configured to achieve a strong, rigid, and safe coupling. Some embodiments may further provide an improved tactile feel for a surgeon or other user. Some embodiments may also be configured to reduce stress on the implant by, for example, reducing or, in some embodiments, eliminating, any point and/or line contacts between the inserter and the implant. This may be particularly useful in embodiments in which the spacer is made up of a ceramic material, since such materials may result in implant weakening or failure due to application of certain point and/or line loads.

Some embodiments may also provide for an improved ability to rotate the spacer in situ. Since such rotations or "flip" maneuvers often result in the application of large forces, and may tend to apply such forces in a point or line contact manner, the resultant stresses on a spinal implant may lead to weakening and/or failure of the implant. Existing inserter/implant interfaces often severely limit the amount of torque that may be effectively applied in this manner by virtue of the fragile nature of the interface and/or the way that the interface causes the forces to be applied (such as in a line and/or contact manner, for example).

Attempts at overcoming such disadvantages have been attempted. However, they have generally resulted in weak or otherwise less than ideal spacer/inserter interfaces that often do not provide a surgeon with a good "feel." In other words, many of the prior art implementations have resulted in a wobbly or otherwise undesirable sensation during use and also often result in undue slippage between the inserter and spacer.

Thus, some embodiments may provide one or more advantages over the prior art by, for example, an interface that conforms to at least a portion of a surface of the implant. For example, the implant may have a rear surface that is shaped to at least substantially mate and/or match a corresponding surface of the inserter. In some embodiments, this shape may comprise a recess. In some such embodiments, this shape may comprise a v-shaped recess, or an at least substantially v-shaped recess. This recess may, in some embodiments, extend along one side of an end wall of a spinal spacer to an opposite side of the end wall. In some embodiments, the recess may extend in a horizontal direction relative to the spacer when placed in an initial, in situ position. In other embodiments, the recess may extend in a vertical direction relative to the spacer when placed in an initial in situ position. Still other embodiments may comprise a recess extending along a diagonal of an end wall surface, or any other suitable direction. Some embodiments may comprise multiple such recesses and a corresponding surface of the inserter may comprise one or more protrusions configured to mate/match and fit within the recess(es) of the implant. For example, some embodiments are contemplated in which two intersecting recesses are formed on the implant (or inserter/intermediary piece). Some such embodiments may be formed in an "X" shape, for example.

Alternatively, as discussed below, one or more intermediary pieces may be provided that are configured to be coupled with an inserter and define the surface to be engaged with the implant. As another alternative, some embodiments are contemplated in which the inserter or intermediary piece comprises a recess and the implant comprises a corresponding protrusion.

Some embodiments may comprise one or more recesses defined by two flat surfaces separated by an angle and an interconnecting curved surface. The two flat surfaces may increase the surface area of contact between an inserter and an implant to reduce application of forces in a point/line contact manner during use. By curving the area of the recess that connects the two flat surfaces, rather than connecting them at a pointed tip, forces concentrated at the tip of the corresponding protrusion on the inserter may be reduced. Some embodiments may be configured with a groove and/or corresponding protrusion lacking any sharp corners, which may further aid in preventing concentrated forces.

However, it should be understood that a pointed surface and/or connecting surfaces that are not flat may suffice for certain embodiments and implementations, depending upon, for example, the materials used and/or the expected uses and resultant forces expected during use. It should be understood that, for purposes of this disclosure, the term "v-shaped recess" may encompass recesses having two flat surfaces with a curved surface connecting the two flat surfaces, even though these surfaces do not come together at a point like a typical letter "V," so long as the two flat surfaces are not parallel to one another as they would be for a "U" shaped recess.

In some embodiments, the portion of the inserter that is configured to engage the implant may comprise a material having a low modulus of elasticity. Such embodiments may be particularly useful in connection with spinal spacers comprising a ceramic material, such as a silicon nitride ceramic. Examples of materials having low moduli of elasticity that may be useful for such embodiments include, for example, plastics, rubber, and certain metals such as gold, titanium, silver, and aluminum.

By providing an interface with a material having a low modulus of elasticity, an inserter may be more suitable for rotating a spacer in situ, or otherwise for application of high torque or other forces, without substantial risk for resulting in weakening and/or failure of the implant. These benefits may be accomplished because use of the interface shapes and/or materials described herein may reduce or eliminate point and/or line forces during use. In some embodiments, the surface configured to interface with a spinal implant may be coated, layered, or otherwise covered with a material having a relatively low modulus of elasticity in order to take advantage of one or more such benefits.

Some embodiments may be configured with an intermediary piece configured to be coupled to an inserter and be positioned between the inserter and the implant. This may provide a convenient way to provide an interface comprising a low-modulus material even if the inserter is made from a material having a high modulus of elasticity, such as steel. In such embodiments, the intermediary piece may be made up of a low-modulus material and may couple with the inserter. The intermediary piece may have one or more protrusions configured to fit within one or more recesses formed in an end wall surface of the implant.

Providing at least one surface of an inserter/implant interface that comprises a material having a low modulus of elasticity may be particularly useful for embodiments comprising a ceramic material, such as a silicon nitride ceramic material.

Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide, and strontium oxide, can be processed to form a doped composition of Silicon Nitride. In some embodiments, powders of silicon nitride may be used to form the ceramic implants, either alone or in combination with one or more of the dopants referenced above. Other examples of suitable silicon nitride materials are described in U.S. Pat. No. 7,666,229 titled "Ceramic-Ceramic Articulation Surface Implants," which is hereby incorporated by reference. Still other examples of suitable Silicon Nitride materials are described in U.S. Pat. No. 7,695,521 titled "Hip Prosthesis with Monoblock Ceramic Acetabular Cup," which is also hereby incorporated by reference.

However, in certain embodiments and implementations, such as embodiments comprising a metal on metal interface between the insertion tool and the spinal implant for example, providing a material having a low modulus of elasticity may be less important, and therefore omitted.

Additional details regarding certain preferred embodiments will now be described in greater detail with reference to the accompanying drawings.

FIG. 1 is a perspective diagram illustrating one exemplary embodiment of the intervertebral implant device 10 of the present invention. In this exemplary embodiment, the intervertebral implant device 10 includes a pair of substantially parallel opposed arcuate surfaces 12 and a pair of substantially parallel opposed frictional surfaces 14 including a plurality of raised structures 16, such as teeth, grooves or the like. The pair of opposed arcuate surfaces 12 and the pair of opposed frictional surfaces 14 together form a prismatic structure that has a slight curve in one plane. This prismatic structure has overall dimensions on the order of tens of mm in length, tens of mm in width, and several mm in thickness, such that it may be disposed in a range of intervertebral spaces and provide a range of distraction, if so desired. Preferably, the prismatic structure defines one or more voids 18 in which a bone graft material or the like may selectively be disposed. These voids 18 may be internal to the prismatic structure, pass through the pair of opposed arcuate surfaces 12, pass through the pair of opposed frictional surfaces 14, and/or be in communication with one or more recesses 19 manufactured into the exterior of the pair of opposed arcuate surfaces 12 and/or the pair of opposed frictional surfaces 14. These voids 18 and/or recesses 19 help promote bony ingrowth that eventually fuses the intervertebral implant device 10 in the intervertebral space. One end of the intervertebral implant device 10 includes a rounded or partially-rounded end wall 20, that preferably has smoothed edges 21 to prevent it from catching on or damaging any anatomical structures during insertion. The other end of the intervertebral implant device 10 includes a recessed or fish-tailed end wall 22. The fish-tailed end wall 22 defines a hole and/or other retention structures 24 for selectively and pivotably receiving one or more surgical implantation devices. In this exemplary embodiment, the fish-tailed end wall 22 includes a pair of angularly disposed walls 23, 25 joined by a central flat wall 27. The first of the pair of angularly disposed walls 23 protrudes from the prismatic structure to a greater degree than the second of the pair of angularly disposed walls 25, although other suitable configurations may be utilized. In this exemplary embodiment, the retention structures 24 for selectively and pivotably receiving one or more surgical implantation devices are coextensive with the one or more recesses 19 manufactured into the exterior of the pair of opposed arcuate surfaces 12 and/or the pair of opposed frictional surfaces 14. The intervertebral implant device 10 may be made of any suitable surgically-implantable material, such as a metallic material, a ceramic material, a polymeric material, or an allograft material, and may have any suitable dimensions such that it may be disposed within an intervertebral space of the spine of a patient while providing a desired degree of distraction. It can also be seen from the figures that the fish-tailed structure occupies at least substantially the entire surface of the fish-tailed end wall 22.

Advantageously, the configuration of the pair of substantially parallel opposed arcuate surfaces 12 and the pair of substantially parallel opposed frictional surfaces 14 provides a surgical implant that may be placed into the intervertebral space through a narrow transforaminal window or the like that is disposed either to the left or the right of the spinal centerline. This is due to the fact that the prismatic structure is symmetric top-to-bottom. Once placed, the plurality of raised structures 16 of the pair of substantially parallel opposed frictional surfaces 14 engage the intervertebral endplates, securing the intervertebral implant device 10 snugly in place.

Figure 2:
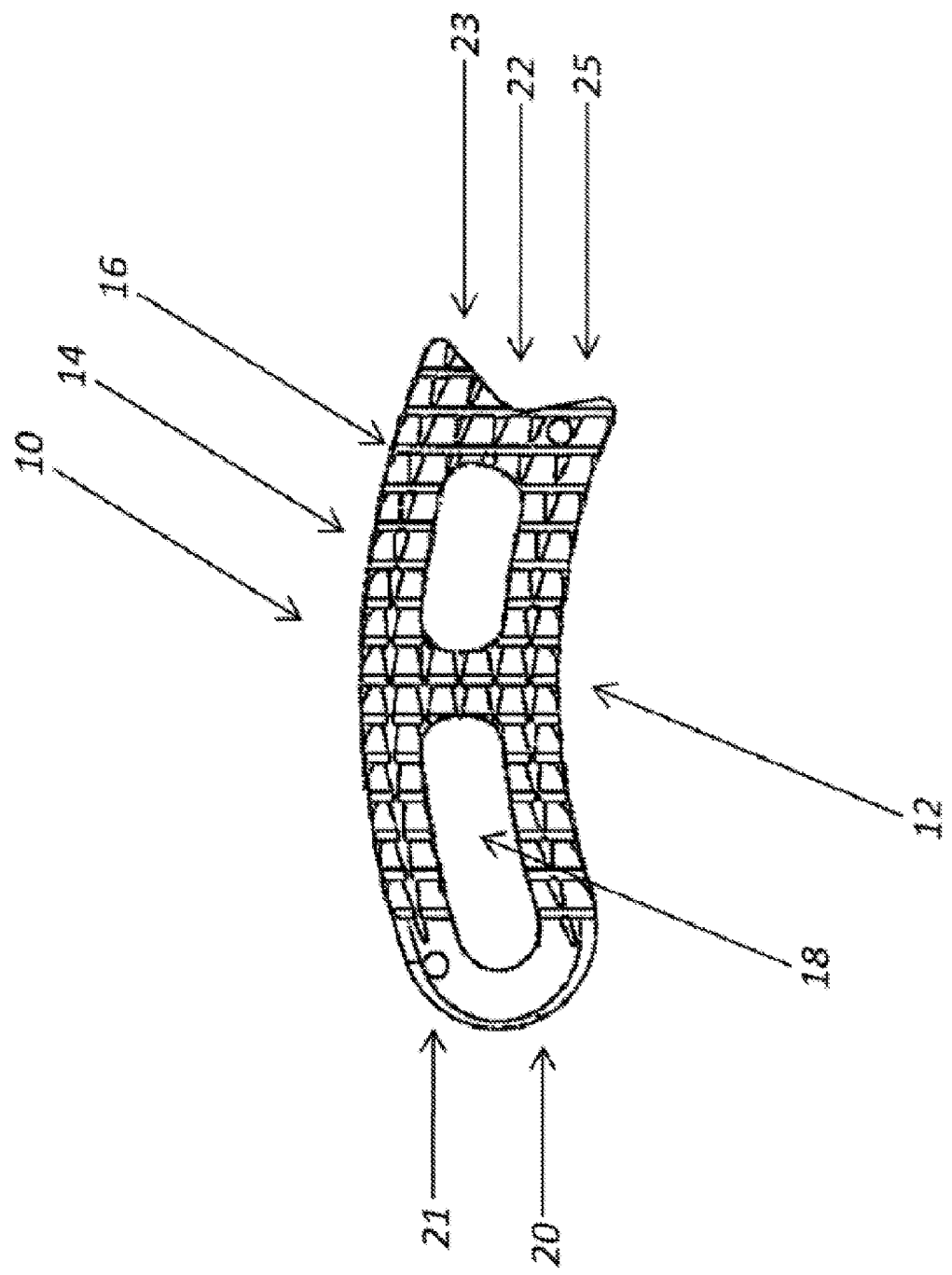
FIG. 2 is a planar diagram also illustrating one exemplary embodiment of the intervertebral implant device.

FIG. 2 is a planar diagram also illustrating one exemplary embodiment of the intervertebral implant device 10 of the present invention. Again, in this exemplary embodiment, the intervertebral implant device 10 includes a pair of substantially parallel opposed arcuate surfaces 12 and a pair of substantially parallel opposed frictional surfaces 14 including a plurality of raised structures 16, such as teeth, grooves or the like. The pair of opposed arcuate surfaces 12 and the pair of opposed frictional surfaces 14 together form a prismatic structure that has a slight curve in one plane. This prismatic structure has overall dimensions on the order of tens of mm in length, tens of mm in width, and several mm in thickness, such that it may be disposed in a range of intervertebral spaces and provide a range of distraction, if so desired. Preferably, the prismatic structure defines one or more voids 18 in which a bone graft material or the like may selectively be disposed. These voids 18 may be internal to the prismatic structure, pass through the pair of opposed arcuate surfaces 12, pass through the pair of opposed frictional surfaces 14, and/or be in communication with one or more recesses 19 (FIG. 1) manufactured into the exterior of the pair of opposed arcuate surfaces 12 and/or the pair of opposed frictional surfaces 14. These voids 18 and/or recesses 19 help promote bony ingrowth that eventually fuses the intervertebral implant device 10 in the intervertebral space. One end of the intervertebral implant device 10 includes a rounded or partially-rounded end wall 20, that preferably has smoothed edges 21 to prevent it from catching on or damaging any anatomical structures during insertion. The other end of the intervertebral implant device 10 includes a recessed or fish-tailed end wall 22. The fish-tailed end wall 22 defines a hole and/or other retention structures 24 (FIG. 1) for selectively and pivotably receiving one or more surgical implantation devices. In this exemplary embodiment, the fish-tailed end wall 22 includes a pair of angularly disposed walls 23, 25 joined by a central flat wall 27 (FIG. 1). The first of the pair of angularly disposed walls 23 protrudes from the prismatic structure to a greater degree than the second of the pair of angularly disposed walls 25, although other suitable configurations may be utilized. In this exemplary embodiment, the retention structures 24 for selectively and pivotably receiving one or more surgical implantation devices are coextensive with the one or more recesses 19 manufactured into the exterior of the pair of opposed arcuate surfaces 12 and/or the pair of opposed frictional surfaces 14. The intervertebral implant device 10 may be made of any suitable surgically-implantable material, such as a metallic material, a ceramic material, a polymeric material, or an allograft material, and may have any suitable dimensions such that it may be disposed within an intervertebral space of the spine of a patient while providing a desired degree of distraction.

Figure 3:
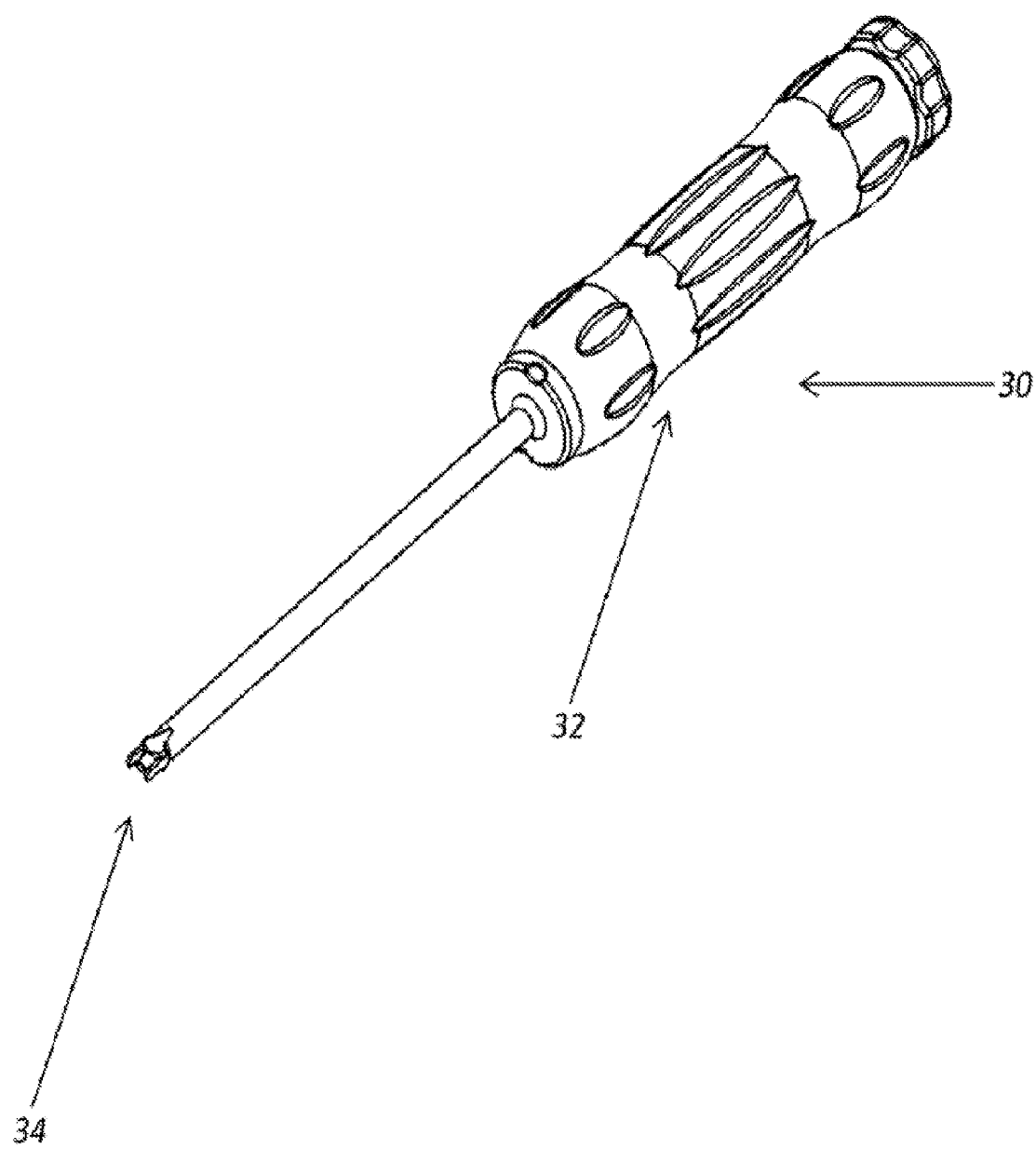
FIG. 3 is a perspective diagram illustrating one exemplary embodiment of a placement device for use with the intervertebral implant device.

FIG. 3 is a perspective diagram illustrating one exemplary embodiment of a placement device 30 for use with the intervertebral implant device 10 (FIGS. 1 and 2) of the present invention. The placement device 30 includes a handle portion 32 and an engaging portion 34. Preferably, the engaging portion 34 includes a pillar and/or fin structures for selectively engaging the hole and/or other retention structures 24 (FIG. 1) of the intervertebral implant device 10, such that the intervertebral implant device 10 is selectively held by the placement device 30 while being inserted into the intervertebral space.

Figure 4:
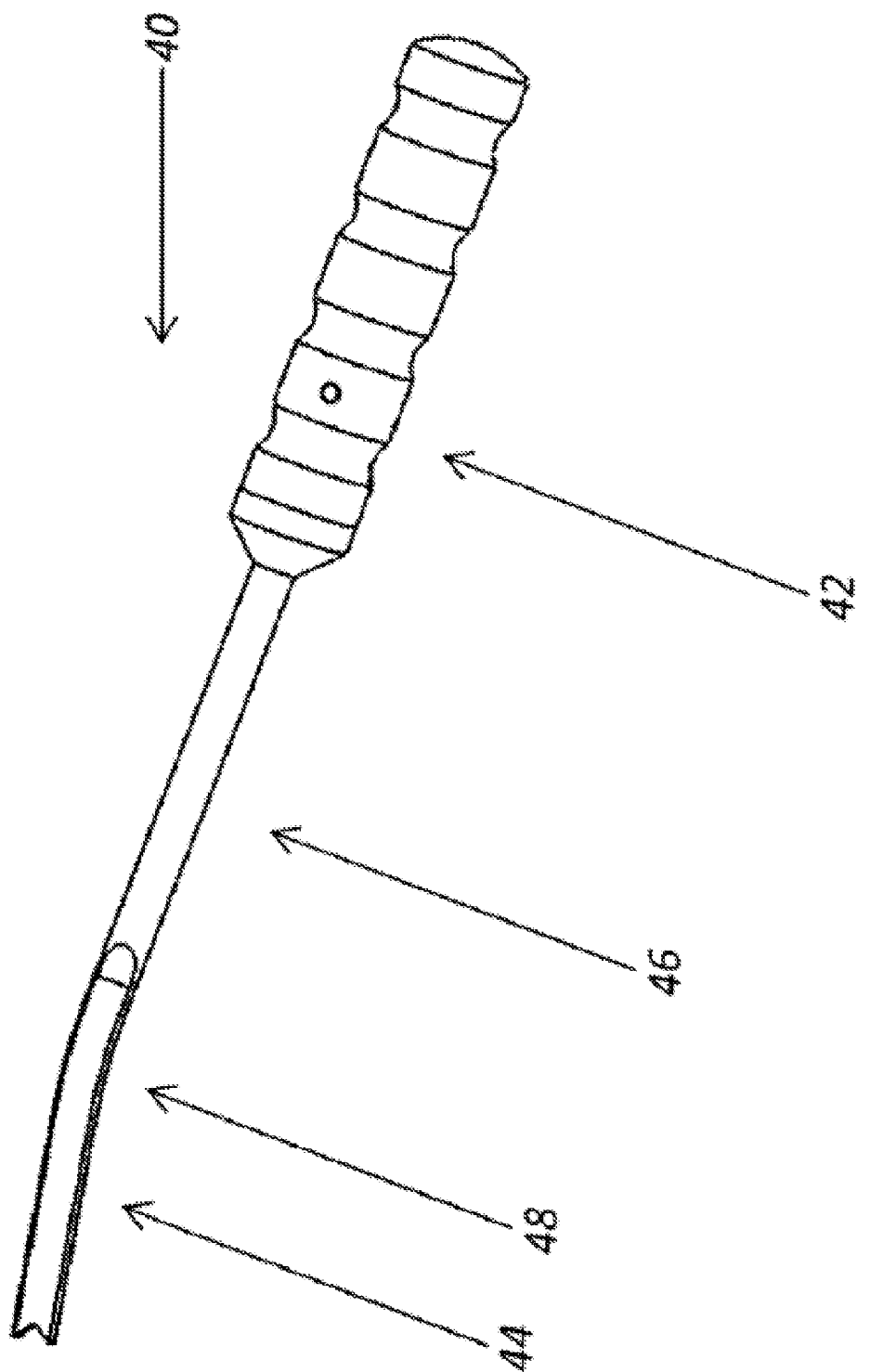
FIG. 4 is a perspective diagram illustrating one exemplary embodiment of a positioning device for use with the intervertebral implant device.

FIG. 4 is a perspective diagram illustrating one exemplary embodiment of a positioning device 40 for use with the intervertebral implant device 10 (FIGS. 1 and 2). The positioning device 40 includes a handle portion 42 and an engaging portion 44. Preferably, the engaging portion 44 includes a fish-tailed feature for selectively engaging the fish-tailed end wall 22 (FIGS. 1 and 2) of the intervertebral implant device 10, such that the intervertebral implant device 10 is selectively guided by the positioning device 40 once inserted into the intervertebral space. Accordingly, the shaft 46 of the positioning device 40 includes a curved portion 48, allowing the positioning device 40 to be guided through a narrow transforaminal window (either left or right) and into the intervertebral space while in contact with the intervertebral implant device 10.

Figure 5:
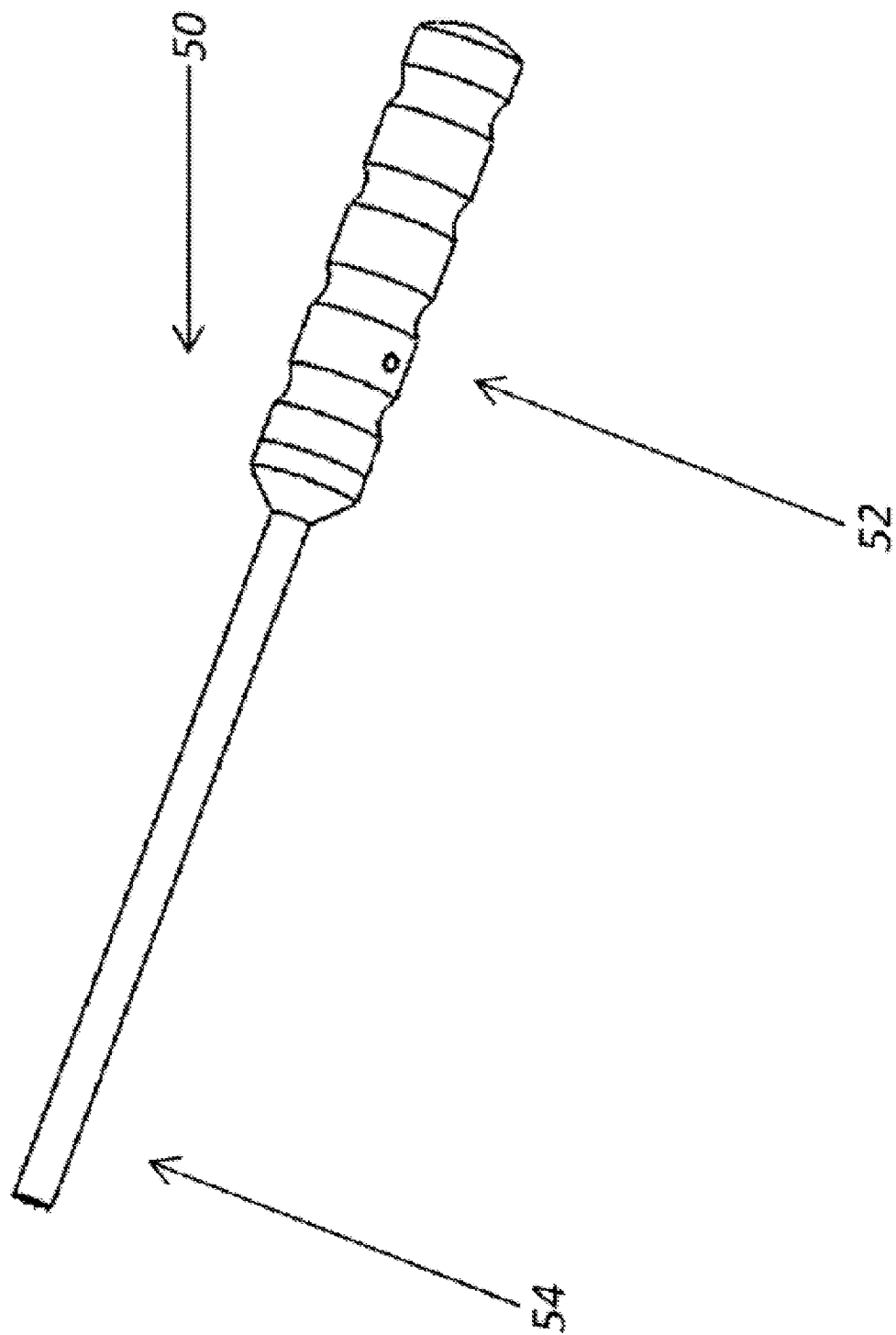
FIG. 5 is a perspective diagram illustrating one exemplary embodiment of a tamping device for use with the intervertebral implant device.

FIG. 5 is a perspective diagram illustrating one exemplary embodiment of a tamping device 50 for use with the intervertebral implant device 10 (FIGS. 1 and 2). The tamping device 50 includes a handle portion 52 and an engaging portion 54. Preferably, the engaging portion 54 includes one or more friction structures for selectively engaging the fish-tailed end wall 22 (FIGS. 1 and 2) of the intervertebral implant device 10, such that the intervertebral implant device 10 is selectively driven by the tamping device 50 while being positioned and seated in the intervertebral space.

Figure 6:
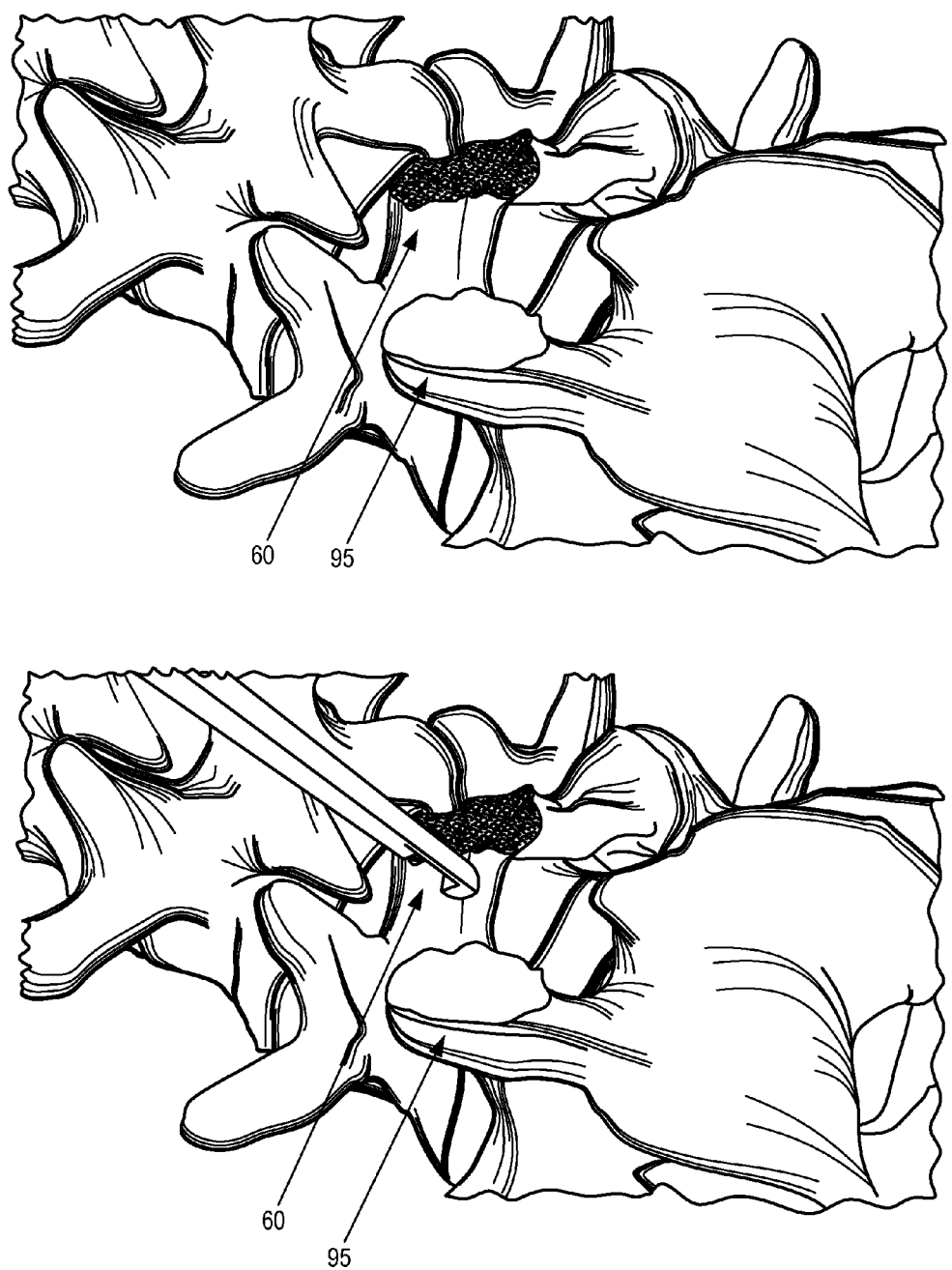
FIG. 6 is a series of perspective drawings illustrating successive steps in one exemplary embodiment of a method for surgically implanting the intervertebral implant device—illustrating the removal of a small amount of bony material adjacent to a facet joint of the spine in order to form an access portal through which the intervertebral implant device of the present invention may be inserted into an intervertebral space.

FIG. 6 is a series of perspective drawings illustrating successive steps in one exemplary embodiment of a method for surgically implanting the intervertebral implant device 10 (FIGS. 1 and 2)—illustrating the removal of a small amount of bony material 60 adjacent to a facet joint 95 of the spine in order to form an access portal through which the intervertebral implant device 10 may be inserted into an intervertebral space.

Figure 7:
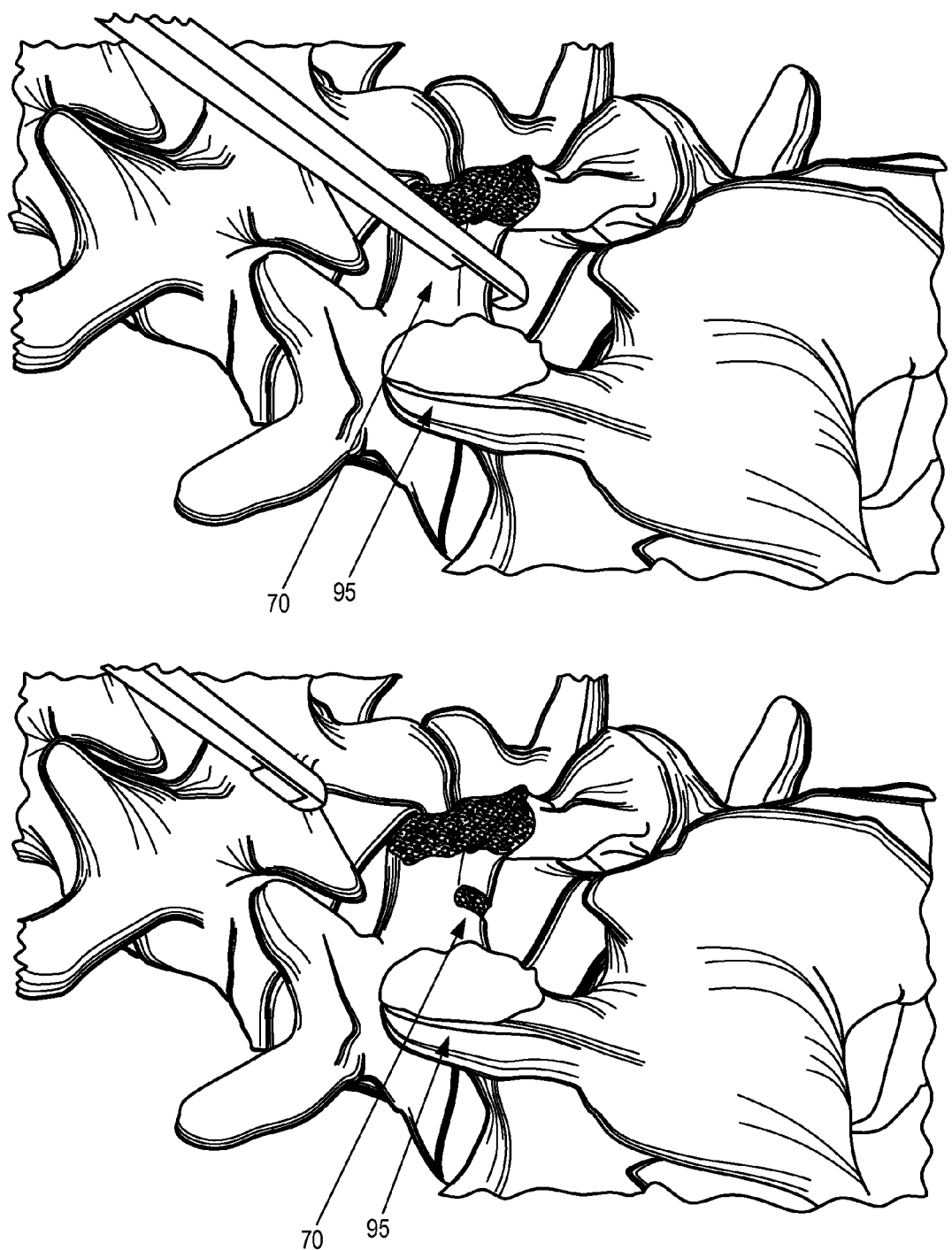
FIG. 7 is a series of perspective drawings illustrating continuing successive steps in one exemplary embodiment of a method for surgically implanting the intervertebral implant device—again illustrating the removal of a small amount of bony material adjacent to a facet joint of the spine in order to form an access portal through which the intervertebral implant device may be inserted into an intervertebral space.

FIG. 7 is a series of perspective drawings illustrating continuing successive steps in one exemplary embodiment of a method for surgically implanting the intervertebral implant device 10 (FIGS. 1 and 2)—again illustrating the removal of a small amount of bony material 70 adjacent to a facet joint 95 of the spine in order to form an access portal through which the intervertebral implant device 10 may be inserted into an intervertebral space.

Figure 8:
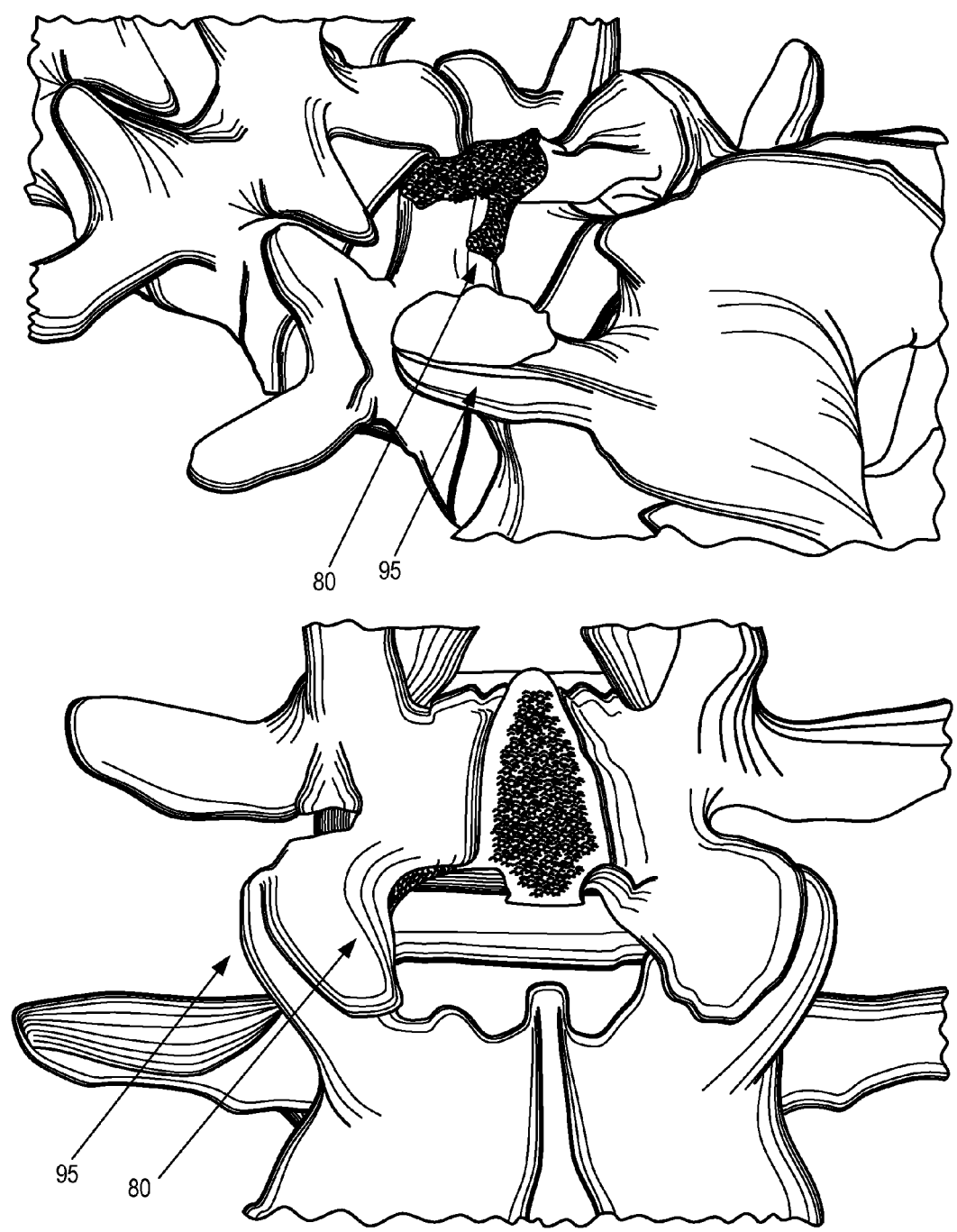
FIG. 8 is a series of perspective drawings illustrating continuing successive steps in one exemplary embodiment of a method for surgically implanting the intervertebral implant device—again illustrating the removal of a small amount of bony material adjacent to a facet joint of the spine in order to form an access portal through which the intervertebral implant device may be inserted into an intervertebral space.

FIG. 8 is a series of perspective drawings illustrating continuing successive steps in one exemplary embodiment of a method for surgically implanting the intervertebral implant device 10 (FIGS. 1 and 2)—again illustrating the removal of a small amount of bony material 80 adjacent to a facet joint 95 of the spine in order to form an access portal through which the intervertebral implant device 10 may be inserted into an intervertebral space.

Figure 9:
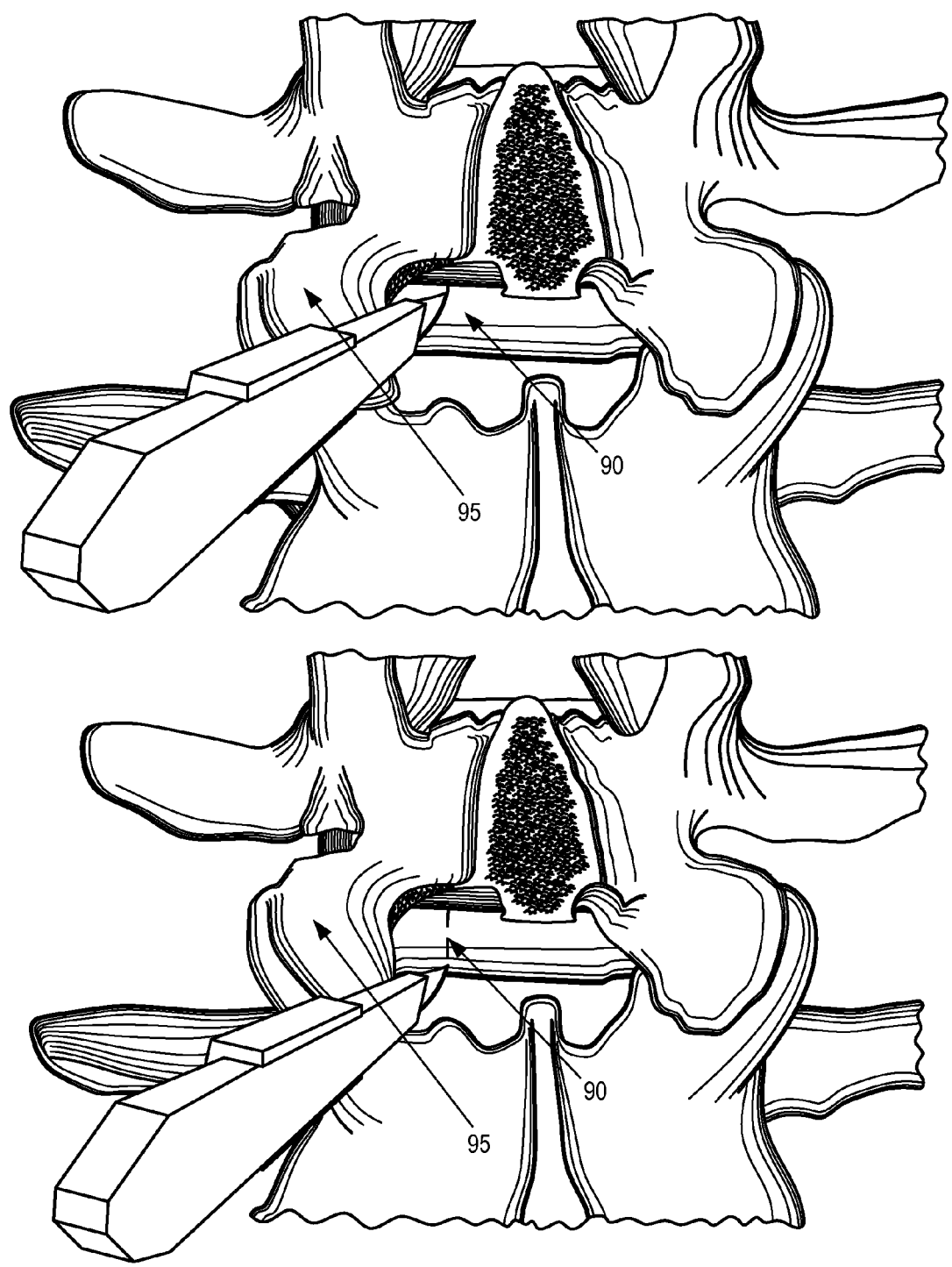
FIG. 9 is a series of perspective drawings illustrating continuing successive steps in one exemplary embodiment of a method for surgically implanting the intervertebral implant device—illustrating the removal of a small amount of soft tissue material adjacent to a facet joint of the spine in order to form an access portal through which the intervertebral implant device may be inserted into an intervertebral space.

FIG. 9 is a series of perspective drawings illustrating continuing successive steps in one exemplary embodiment of a method for surgically implanting the intervertebral implant device 10 (FIGS. 1 and 2)—illustrating the removal of a small amount of soft tissue material 90 adjacent to a facet joint 95 of the spine in order to form an access portal through which the intervertebral implant device 10 may be inserted into an intervertebral space.

Figure 10:
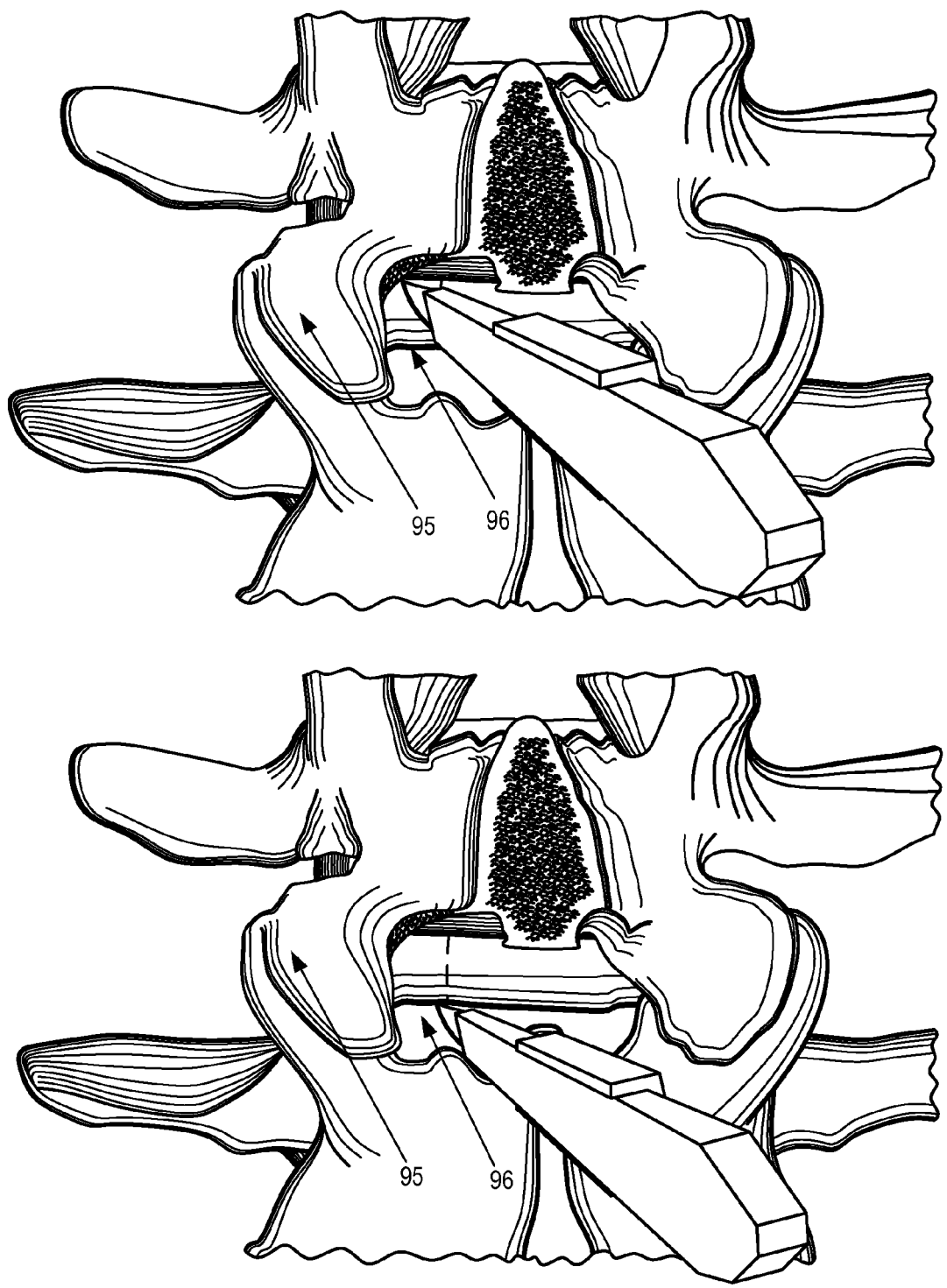
FIG. 10 is a series of perspective drawings illustrating continuing successive steps in one exemplary embodiment of a method for surgically implanting the intervertebral implant device—again illustrating the removal of a small amount of soft tissue material adjacent to a facet joint of the spine in order to form an access portal through which the intervertebral implant device may be inserted into an intervertebral space.

FIG. 10 is a series of perspective drawings illustrating continuing successive steps in one exemplary embodiment of a method for surgically implanting the intervertebral implant device 10 (FIGS. 1 and 2)—again illustrating the removal of a small amount of soft tissue material 96 adjacent to a facet joint 95 of the spine in order to form an access portal through which the intervertebral implant device 10 may be inserted into an intervertebral space.

Figure 11:
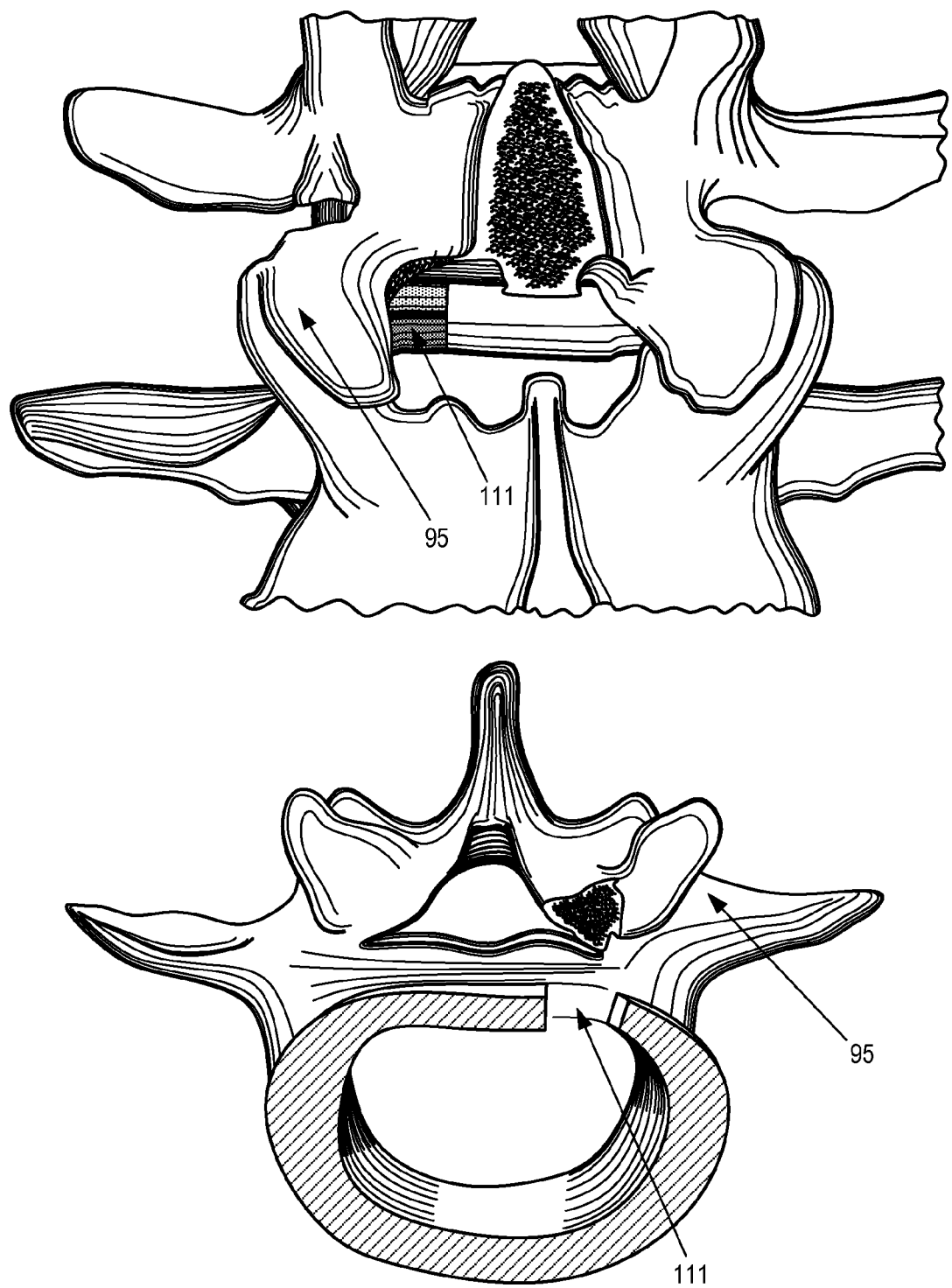
FIG. 11 is a series of perspective drawings illustrating continuing successive steps in one exemplary embodiment of a method for surgically implanting the intervertebral implant device—again illustrating the removal of a small amount of soft tissue material adjacent to a facet joint of the spine in order to form an access portal through which the intervertebral implant device may be inserted into an intervertebral space.

FIG. 11 is a series of perspective drawings illustrating continuing successive steps in one exemplary embodiment of a method for surgically implanting the intervertebral implant device 10 (FIGS. 1 and 2)—again illustrating the removal of a small amount of soft tissue material 111 adjacent to a facet joint 95 of the spine in order to form an access portal through which the intervertebral implant device 10 may be inserted into an intervertebral space.

Figure 12:
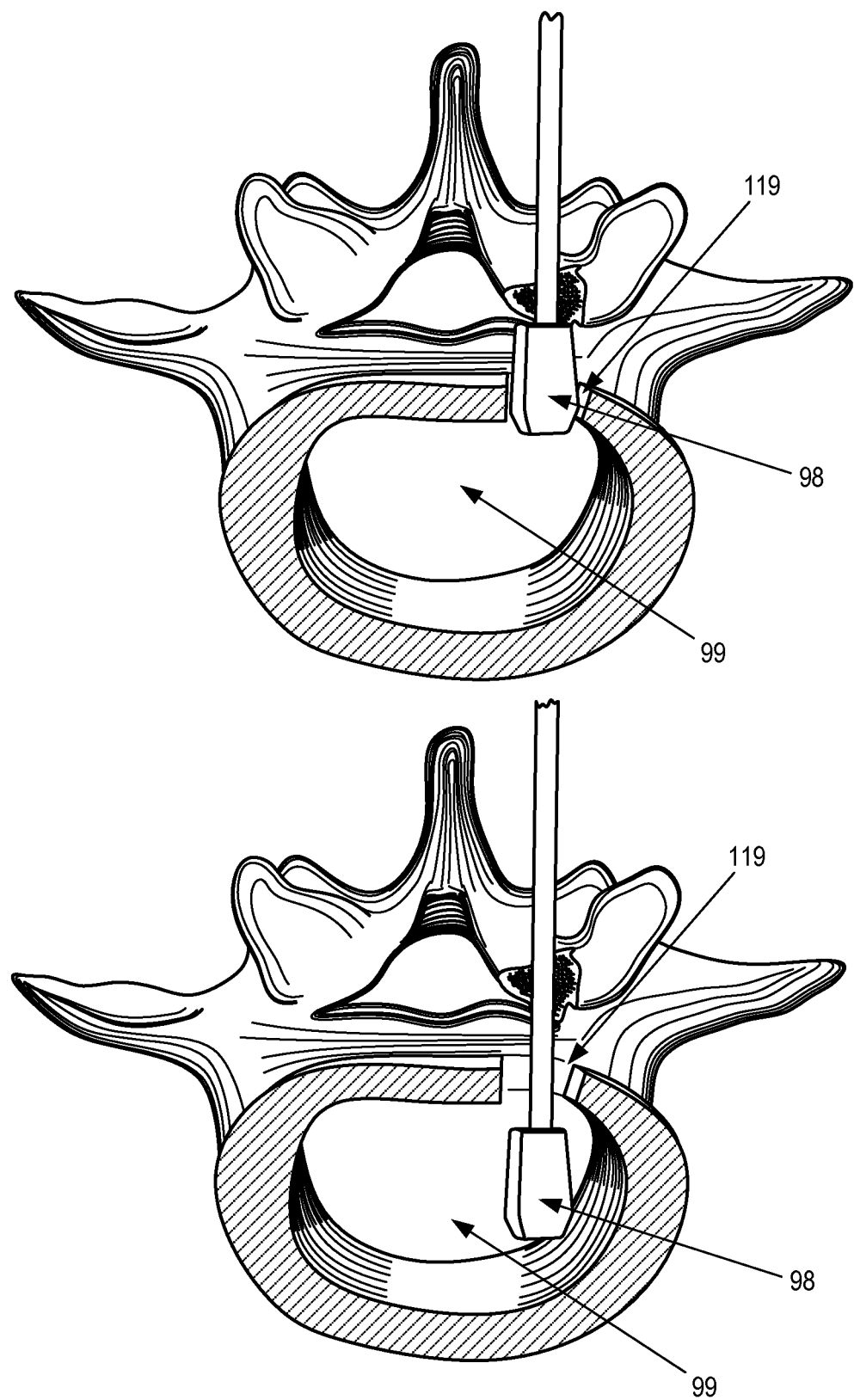
FIG. 12 is a series of perspective drawings illustrating continuing successive steps in one exemplary embodiment of a method for surgically implanting the intervertebral implant device—illustrating the sizing of the intervertebral space prior to the insertion of the intervertebral implant device.

FIG. 12 is a series of perspective drawings illustrating continuing successive steps in one exemplary embodiment of a method for surgically implanting the intervertebral implant device 10 (FIGS. 1 and 2)—illustrating the sizing of the narrow transforaminal window 119 and intervertebral space 99 using a sizing device 98 prior to the insertion of the intervertebral implant device 10.

Figure 13:
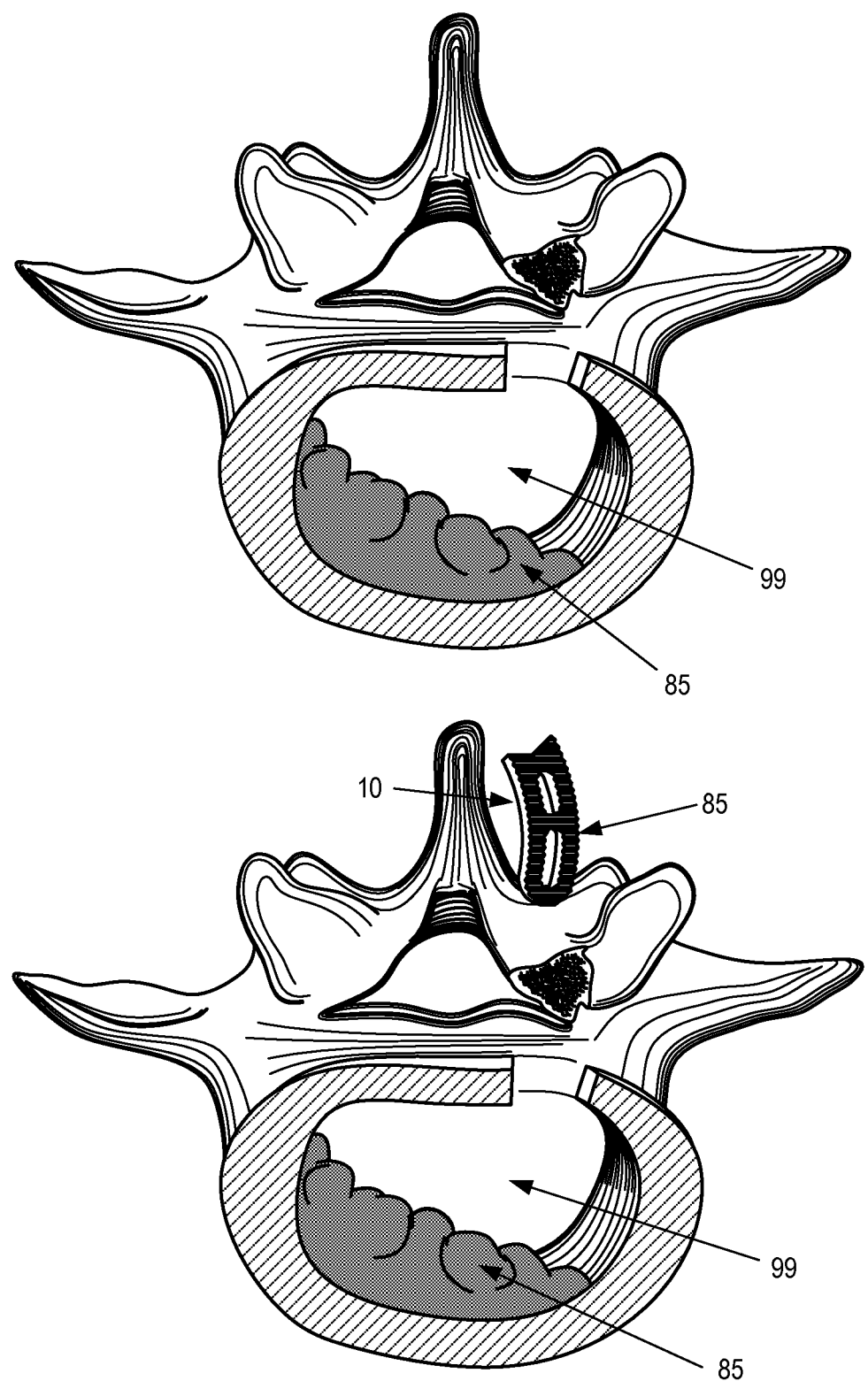
FIG. 13 is a series of perspective drawings illustrating continuing successive steps in one exemplary embodiment of a method for surgically implanting the intervertebral implant device—illustrating the insertion of bone graft material into the intervertebral space prior to the insertion of the intervertebral implant device.

FIG. 13 is a series of perspective drawings illustrating continuing successive steps in one exemplary embodiment of a method for surgically implanting the intervertebral implant device 10—illustrating the insertion of bone graft material 85 into the intervertebral space 99 prior to the insertion of the intervertebral implant device 10. In this exemplary embodiment, the intervertebral implant device is also packed with bone graft material 85.

Figure 14:
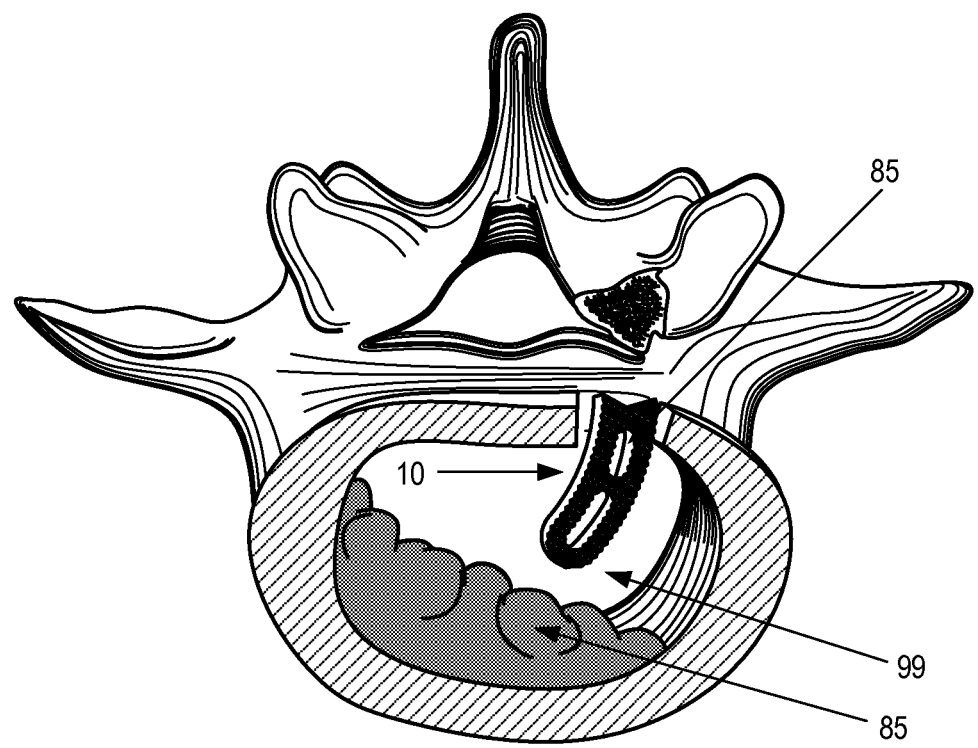
FIG. 14 is a series of perspective drawings illustrating continuing successive steps in one exemplary embodiment of a method for surgically implanting the intervertebral implant device—illustrating the insertion of the intervertebral implant device of the present invention into the intervertebral space using the placement device.
Figure 14:
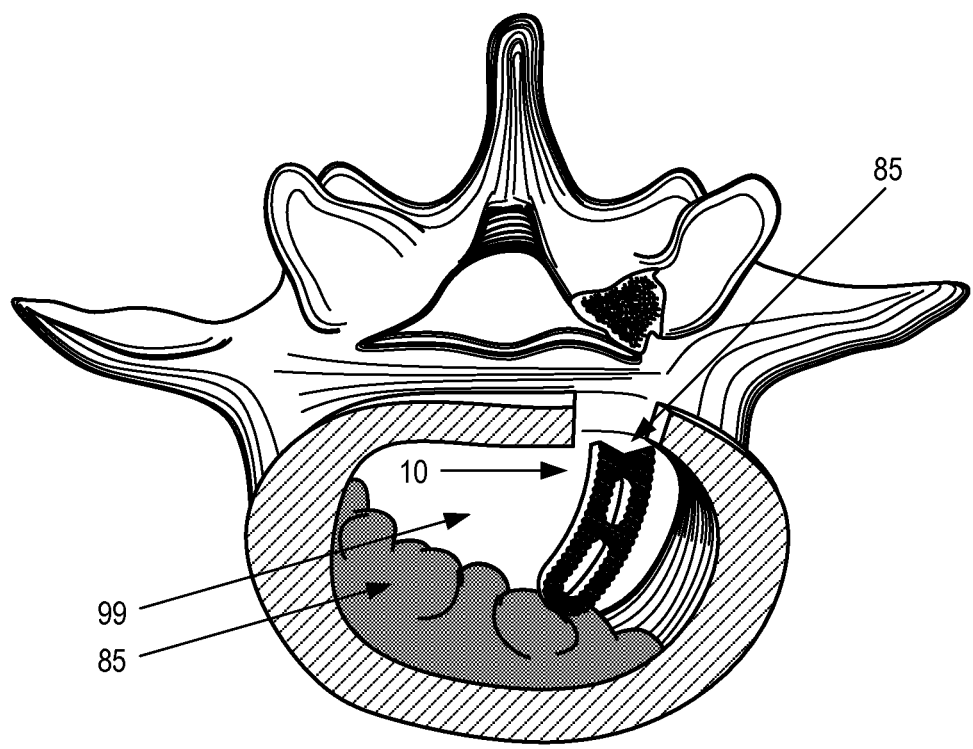

FIG. 14 is a series of perspective drawings illustrating continuing successive steps in one exemplary embodiment of a method for surgically implanting the intervertebral implant device 10—illustrating the insertion of the intervertebral implant device 10 of the present invention into the intervertebral space 99 using the placement device 30 (FIG. 3), for example.

Figure 15:
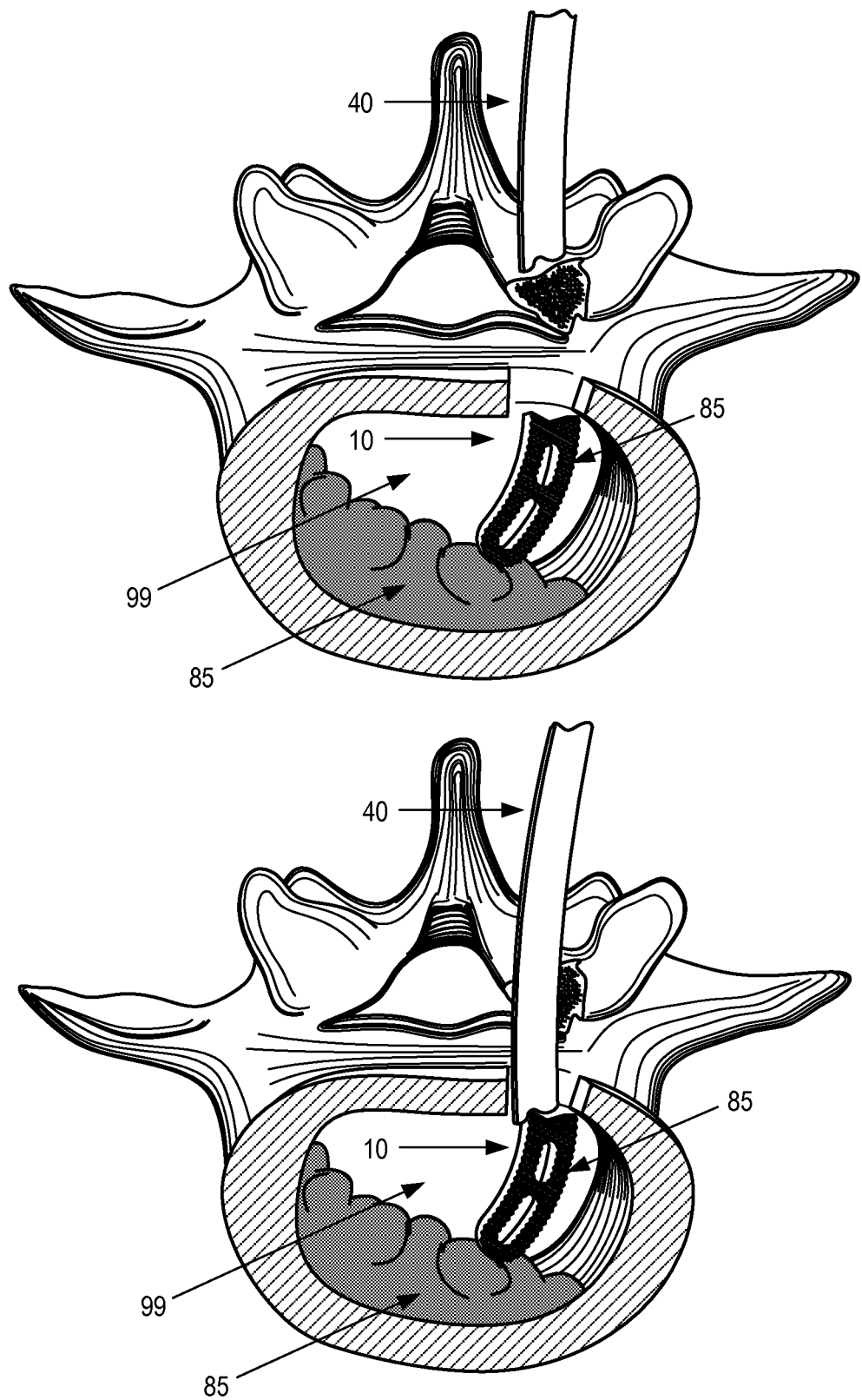
FIG. 15 is a series of perspective drawings illustrating continuing successive steps in one exemplary embodiment of a method for surgically implanting the intervertebral implant device—illustrating the insertion and positioning of the intervertebral implant device of the present invention into and within the intervertebral space using the positioning device.

FIG. 15 is a series of perspective drawings illustrating continuing successive steps in one exemplary embodiment of a method for surgically implanting the intervertebral implant device 10—illustrating the insertion and positioning of the intervertebral implant device 10 into and within the intervertebral space 99 using the positioning device 40.

Figure 16:
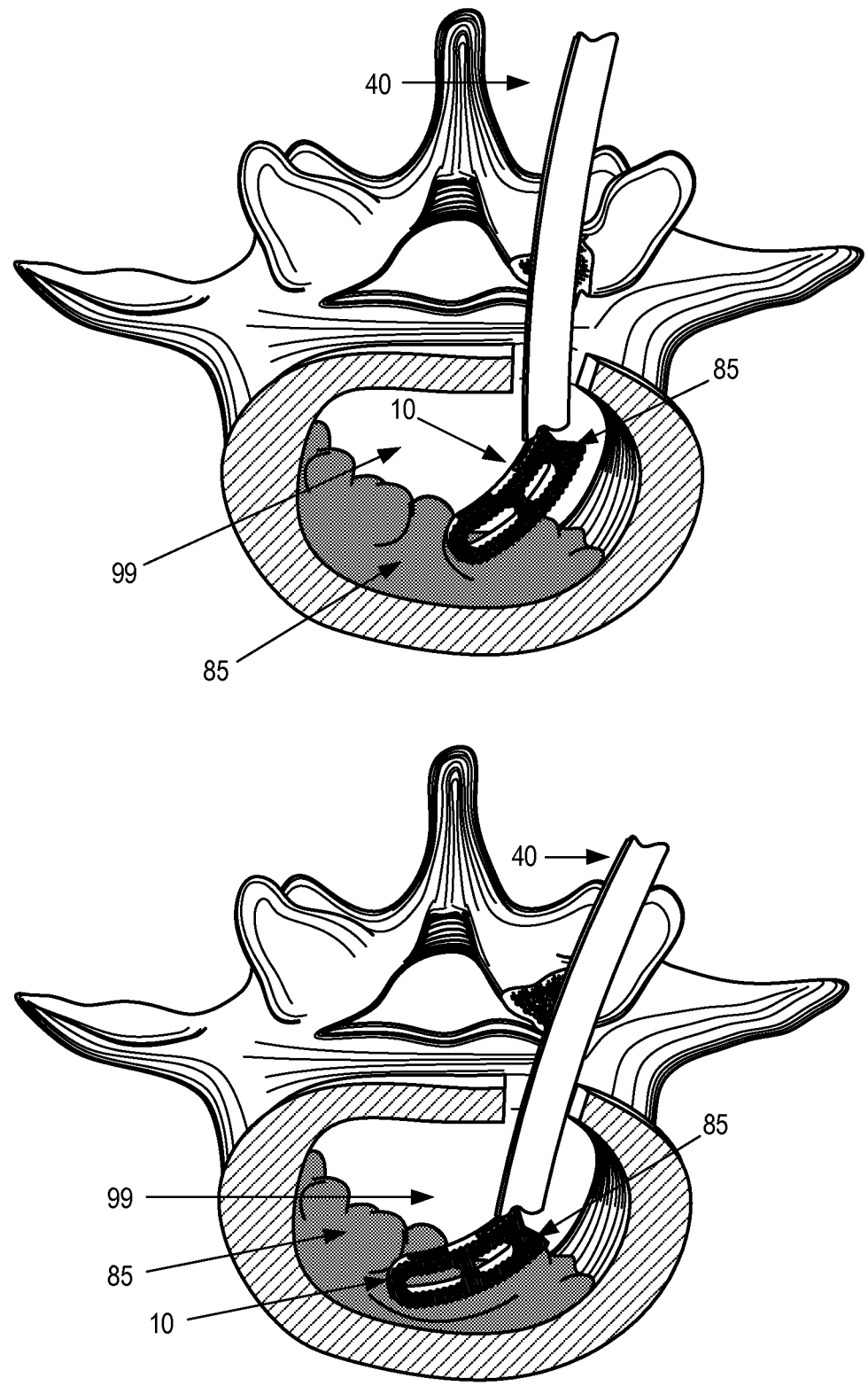
FIG. 16 is a series of perspective drawings illustrating continuing successive steps in one exemplary embodiment of a method for surgically implanting the intervertebral implant device—again illustrating the insertion and positioning of the intervertebral implant device of the present invention into and within the intervertebral space using the positioning device.

FIG. 16 is a series of perspective drawings illustrating continuing successive steps in one exemplary embodiment of a method for surgically implanting the intervertebral implant device 10—again illustrating the insertion and positioning of the intervertebral implant device 10 into and within the intervertebral space 99 using the positioning device 40.

Figure 17:
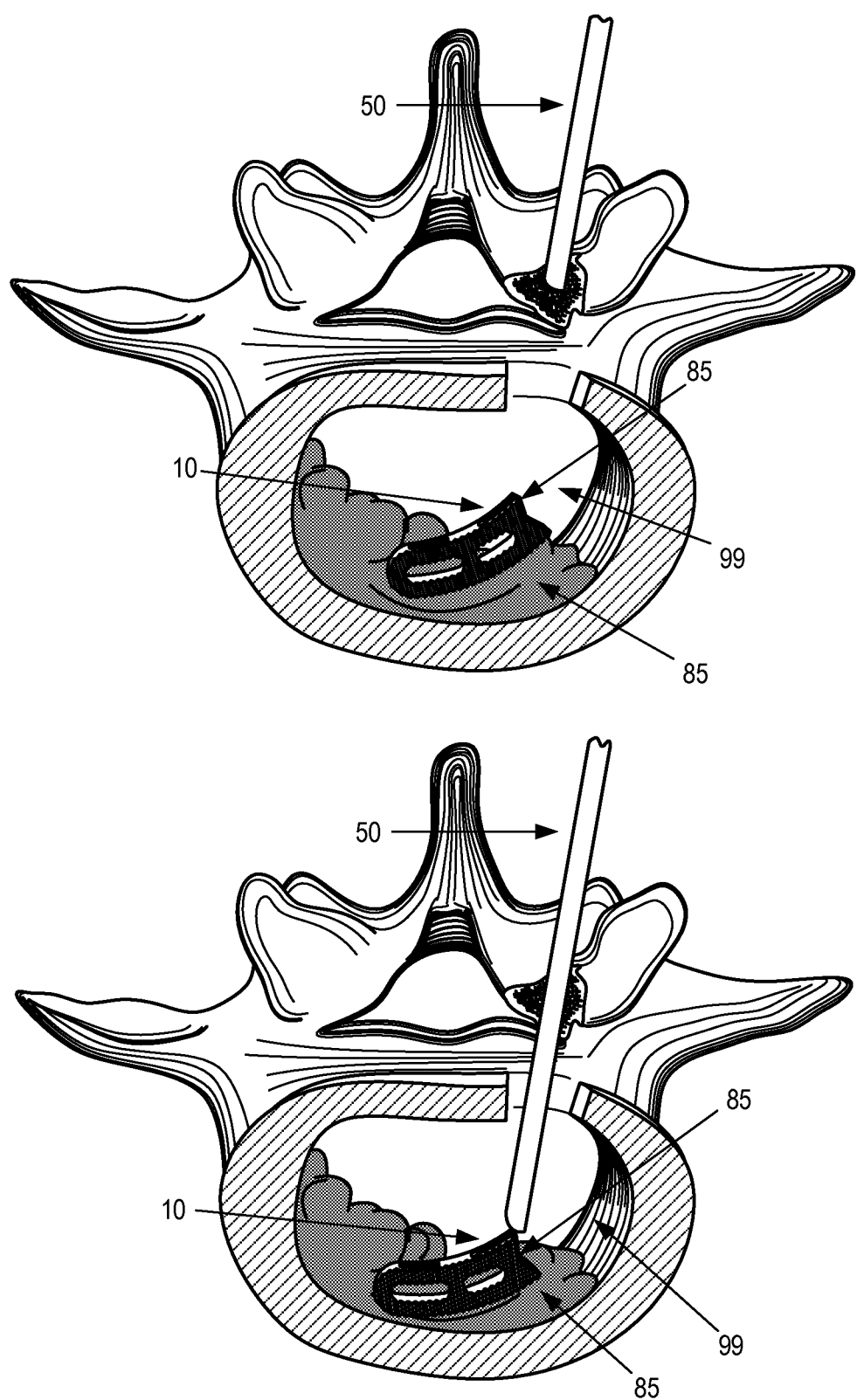
FIG. 17 is a series of perspective drawings illustrating continuing successive steps in one exemplary embodiment of a method for surgically implanting the intervertebral implant device—illustrating the insertion and positioning of the intervertebral implant device into and within the intervertebral space using a tamping device.

FIG. 17 is a series of perspective drawings illustrating continuing successive steps in one exemplary embodiment of a method for surgically implanting the intervertebral implant device 10—illustrating the insertion and positioning of the intervertebral implant device 10 into and within the intervertebral space 99 using the tamping device 50.

Figure 18:
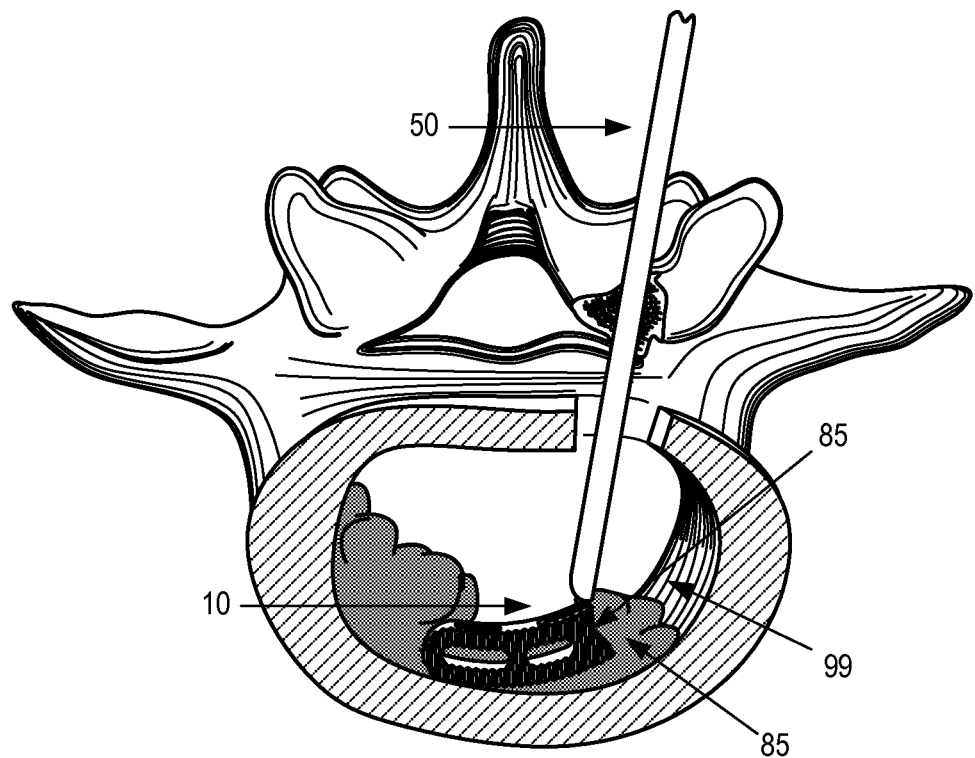
FIG. 18 is a series of perspective drawings illustrating continuing successive steps in one exemplary embodiment of a method for surgically implanting the intervertebral implant device—again illustrating the insertion and positioning of the intervertebral implant device of the present invention into and within the intervertebral space again using the tamping device.
Figure 18:
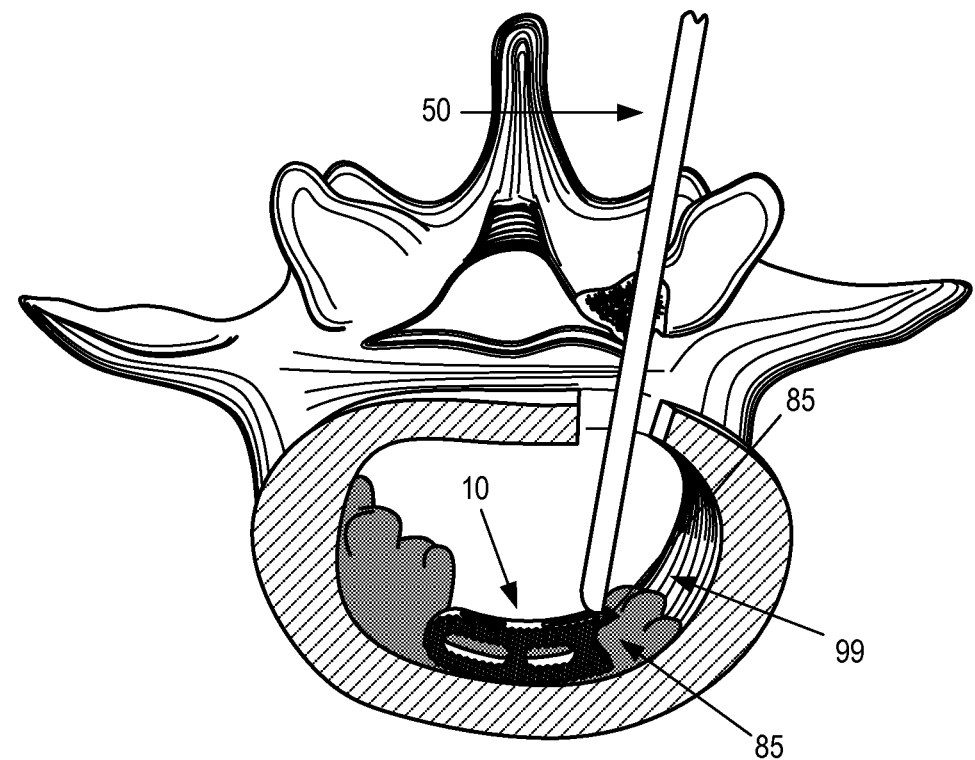

FIG. 18 is a series of perspective drawings illustrating continuing successive steps in one exemplary embodiment of a method for surgically implanting the intervertebral implant device 10—again illustrating the insertion and positioning of the intervertebral implant device 10 into and within the intervertebral space 99 again using the tamping device 50.

Figure 19:
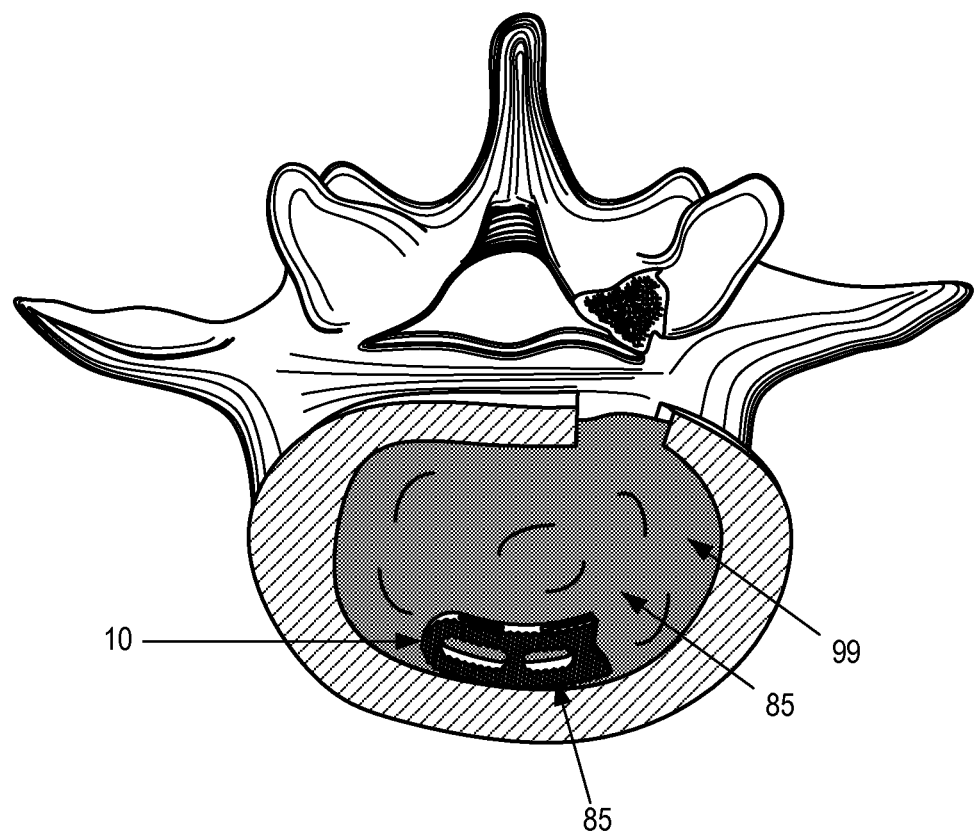
FIG. 19 is a final perspective drawing illustrating a continuing successive step in one exemplary embodiment of a method for surgically implanting the intervertebral implant device—illustrating the final placement of the intervertebral implant device in the intervertebral space, along with the associated bone graft material.

FIG. 19 is another perspective drawing illustrating a continuing successive step in one exemplary embodiment of a method for surgically implanting the intervertebral implant device 10—illustrating the final placement of the intervertebral implant device 10 in the intervertebral space 99, along with the associated bone graft material 85.

Figure 20:
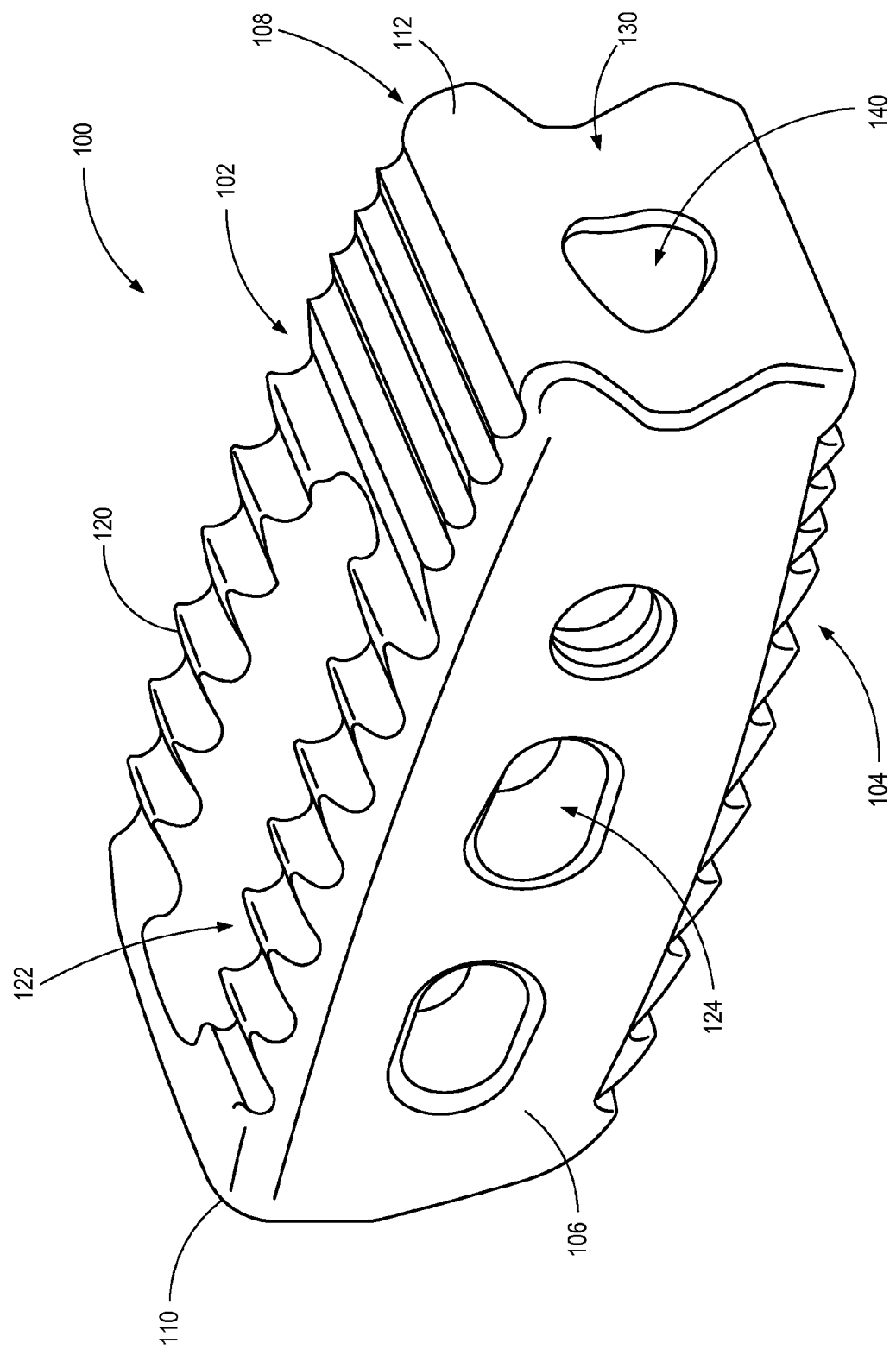
FIG. 20 is a perspective view of a spinal implant according to one embodiment.

FIG. 20 depicts a perspective view of an embodiment of a spinal spacer 100. Spacer 100 comprises an upper surface 102, a lower surface 104, a first side wall surface 106, a second side wall surface 108 opposite from surface 106, a front end wall surface 110, and a rear end wall surface 112 opposite from front end wall surface 110. Upper and lower surfaces 102 and 104 may both comprise a plurality of teeth 120. Upper surface 102 also comprises an opening 122 allowing access to a hollow interior. In some embodiments, lower surface 104 may also have one or more similar openings to allow for bony ingrowth into the interior of spacer 100. Similarly, one or more openings, such as openings 124, may be formed in one or both of side wall surfaces 106/108. Rear end wall surface 112 comprises a recess 130 that is configured to engage a corresponding surface of an inserter tool, as discussed in greater detail below. Recess 130 comprises a fish-tailed recess that, as depicted in FIG. 21, occupies at least substantially the entire surface of rear end wall 112.

As also shown in FIG. 20, spacer 100 may have an opening 140 formed in rear end wall surface 112. In some embodiments, opening 140 may be threaded so as to allow for engagement with an inserter tool, as discussed below. In some embodiments, such as the embodiment depicted in FIG. 20, opening 140 may be formed within recess 130.

Although, as also depicted in FIG. 20, in some embodiments the recess 130 or the fish-tailed structure is formed so as to be visible in a side elevation view (in other words, the recess extends along the entire width of rear end wall surface 112 from the first side wall surface 106 to the second side wall surface 108, other embodiments are contemplated in which recess 130 is formed along a plane perpendicular to that depicted in FIG. 20. In other words, the recess may extend along the entire height of rear end wall surface 112 from the lower surface 104 to the upper surface 102, if desired, such that the recess/fishtail structure is visible from a top plan view perspective.

Figure 21:
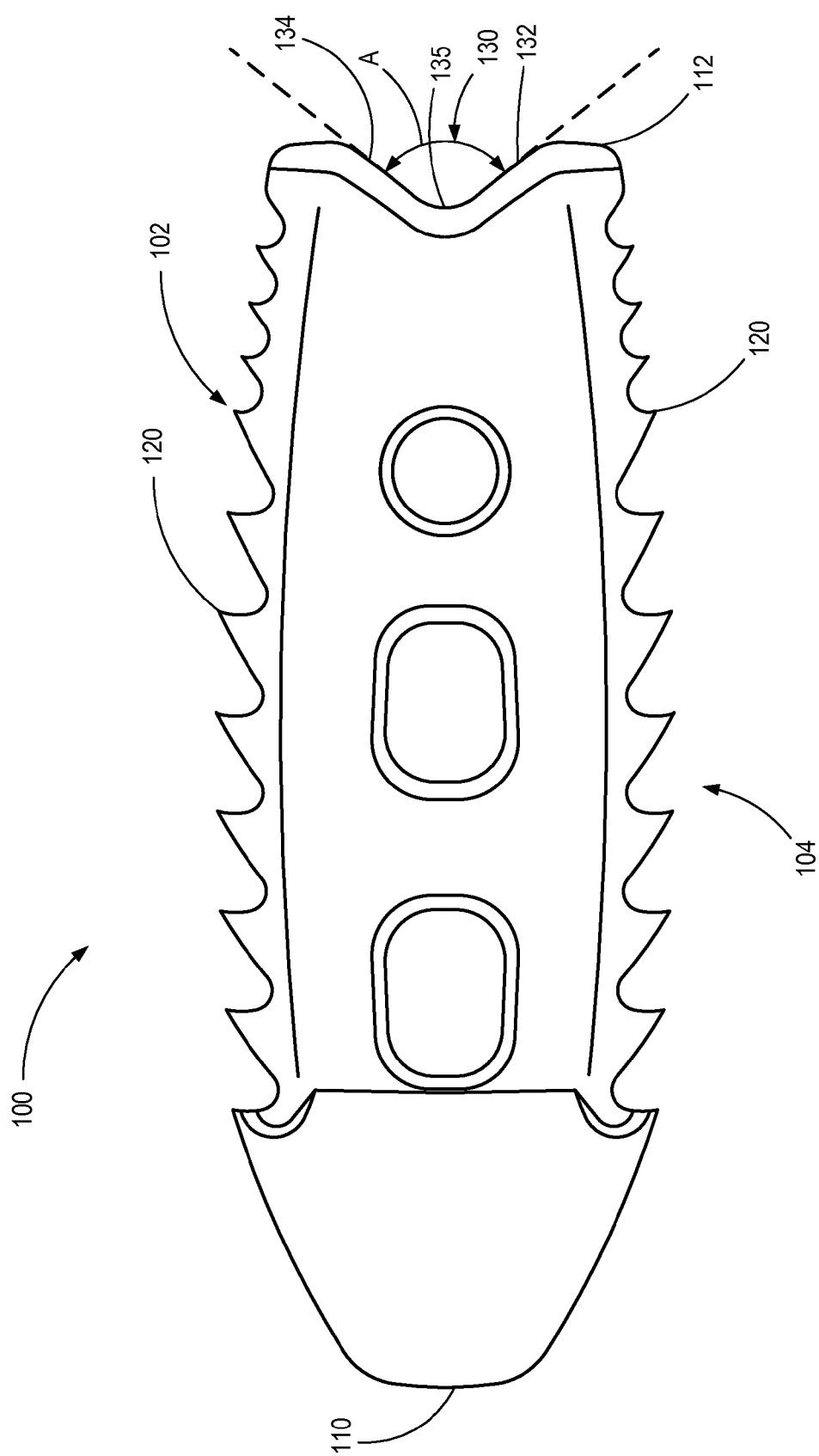
FIG. 21 is a side elevation view of the spinal implant of FIG. 1.

FIG. 21 depicts a side elevation view of spacer 100. As shown in this figure, recess 130 is formed with two at least substantially flat surfaces—surfaces 132 and 134—along with a curved surface 135 that interconnects the two flat surfaces 132 and 134. As also depicted in FIG. 21, surface 132 extends from surface 134 at angle A. In certain preferred embodiments, angle A may be between about 90 degrees and about 120 degrees. In some such embodiments, angle A may be between about 100 degrees and about 110 degrees.

Although, as mentioned above, it may be most preferred to have angle A be within a rather narrow window of angles, and also may be preferred to have angle A be such that the rear end wall surface 112 comprises a recess, other embodiments are contemplated that may still provide benefits over the prior art. For example, in some embodiments, angle A may be between about 5 degrees and about 175 degrees. In some embodiments, angle A may also, or alternatively, be between about 185 degrees and about 355 degrees. In other words, instead of comprising a recess, rear end wall surface 112 may comprise a protrusion. In addition, as described elsewhere in this disclosure, in some embodiments, the recess or protrusion on rear end wall surface 112 may be formed so as to be visible when viewed from the upper surface 102 rather than from the side as depicted in FIG. 21. As long as the corresponding inserter is formed with a mating shape, certain benefits may be derived.

For example, many of the embodiments disclosed herein may allow for transferring a torsional load to an implant, such as a spinal implant, without requiring any engagement with any side of the implant other than the proximal or rear end wall surface. By providing a recess/protrusion interface between the implant and the inserter (or an intermediary piece of the inserter), the need for providing arms, prongs, etc., that extend around the sides, top, and/or bottom surfaces of the implant may be eliminated.

In embodiments, such as that depicted in FIG. 21, comprising a recess defined by two flat surfaces separated by an angle and a connecting curved surface, the two flat surfaces may increase the surface area of contact between an inserter and an implant to reduce application of forces in a point/line contact manner. By curving the area of the recess that connects the two flat surfaces rather than connecting them at a pointed tip, forces concentrated at the tip of the corresponding protrusion on the inserter may be reduced. In addition, it should be understood that recess 130 comprises a "V-shaped" recess for purposes of this disclosure, despite the presence of curved portion 135.

Recesses comprising non-parallel, intersecting flat surfaces may therefore be considered "V-shaped." U-shaped recesses comprising parallel surfaces may also be utilized for some embodiments. However, such embodiments may be less than ideal for certain applications and implementations. For example, a V-shaped recess may allow for use of recess-forming tools having less tight tolerances than a U-shaped recess typically would. V-shaped recesses may also allow for use of a single formation tool for a variety of different sized implants. In some embodiments and implementations, the tool may therefore be configured to form identical curved surfaces for each of a variety of different sized/shaped implants, with only the lengths of the flat surfaces differing.

Figure 22:
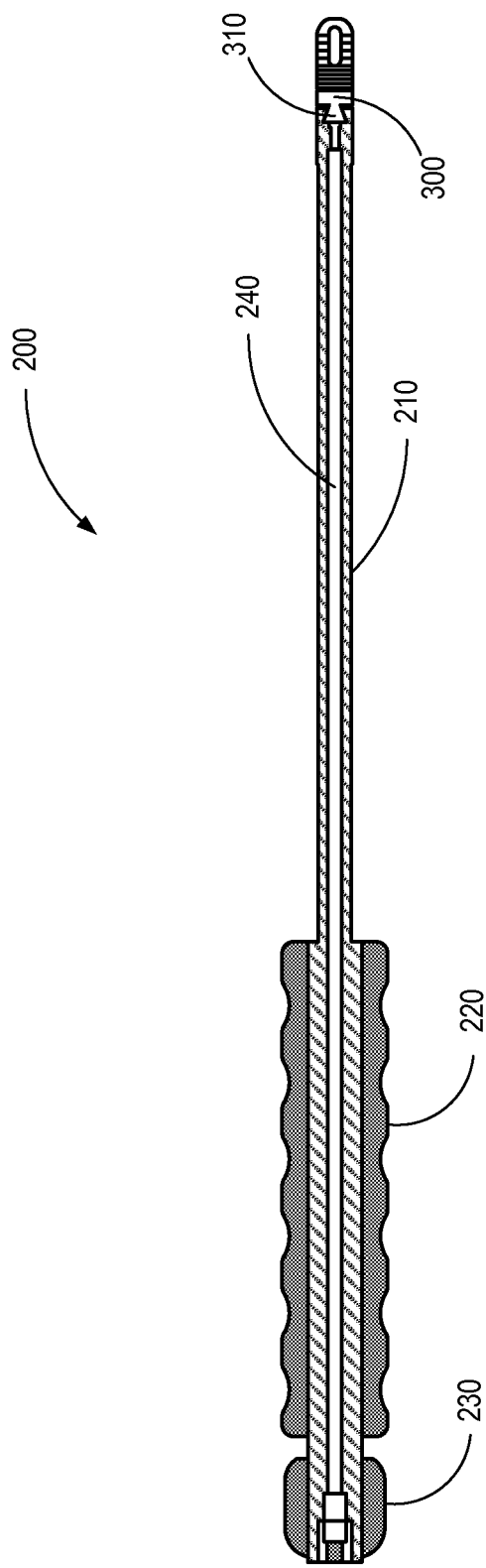
FIG. 22 is a cross-sectional view of an inserter tool for installing a spinal implant according to one embodiment.

FIG. 22 depicts a cross-sectional view of an embodiment of an inserter 200. Inserter 200 comprises a shaft 210, a handle 220, and a handle tip 230. Shaft 210 may have a hollow center 240. Hollow center 240 may be configured to receive a solid inner shaft piece (not shown in the figure) therethrough. The solid inner shaft piece may be configured to couple directly with spinal implant 100. Alternatively, as shown in the embodiment of FIG. 22, the solid inner shaft piece may be configured to extend through an intermediary piece 300 that is, in turn, configured to engage surface 112 of implant 100. In some embodiments, the inner shaft piece may be configured to also extend into implant 100 to solidify the engagement between the inserter 200 and the implant 100. In some embodiments, this may be accomplished by way of a threaded interface.

As also depicted in FIG. 22, intermediary piece 300 may comprise a protrusion 310 that is configured to be received within a corresponding reciprocally shaped recess in inserter 200. Intermediary piece 300 may also have another protrusion on a side of intermediary piece opposite from protrusion 310. This protrusion is best seen in FIGS. 23 and 24, as discussed below, and may be configured to couple with a groove formed within spinal implant 100.

Figure 23:
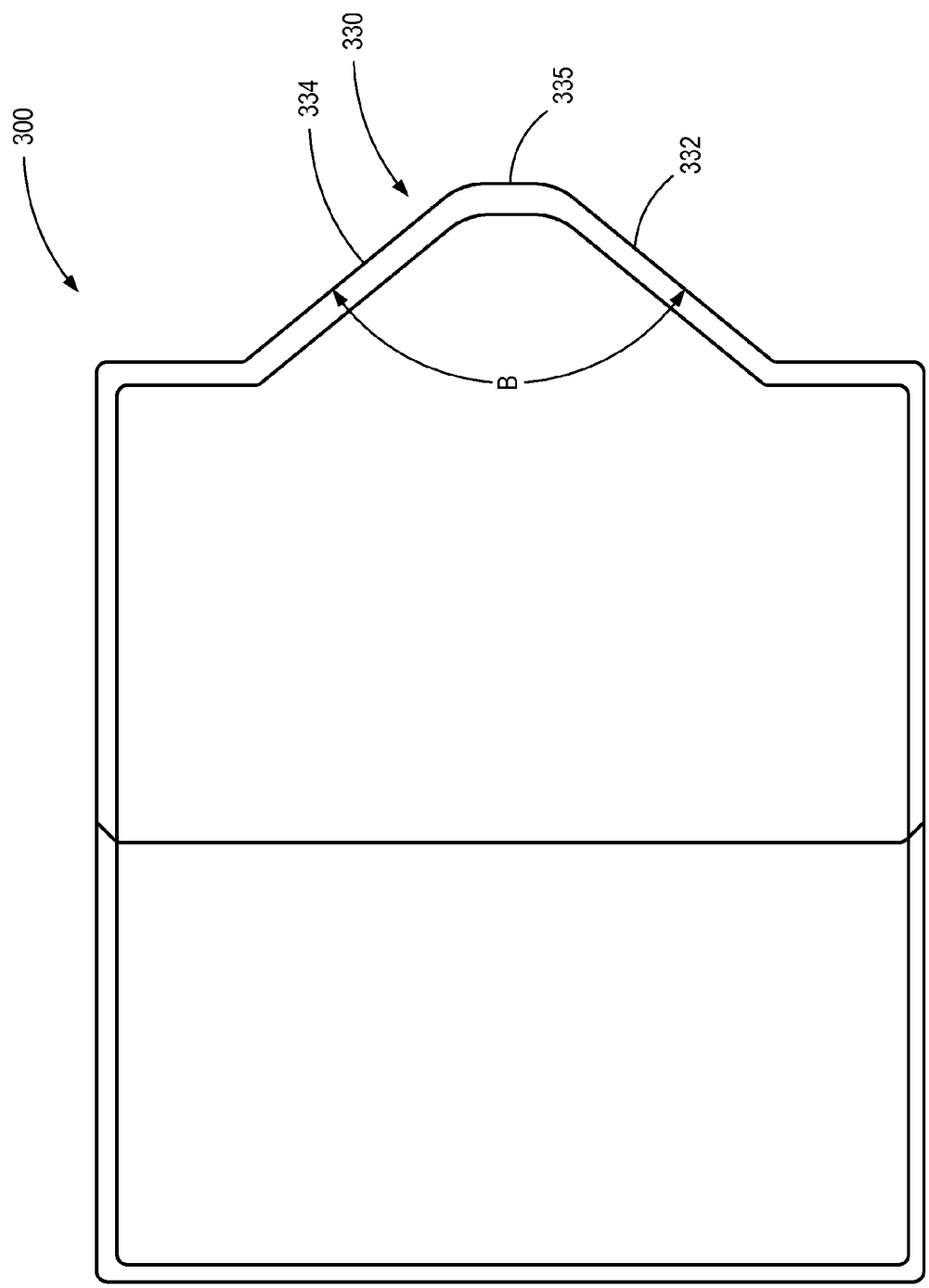
FIG. 23 is a side elevation view of an intermediary piece for placement between, and engagement with, an inserter tool and a spinal implant according to one embodiment.
Figure 24:
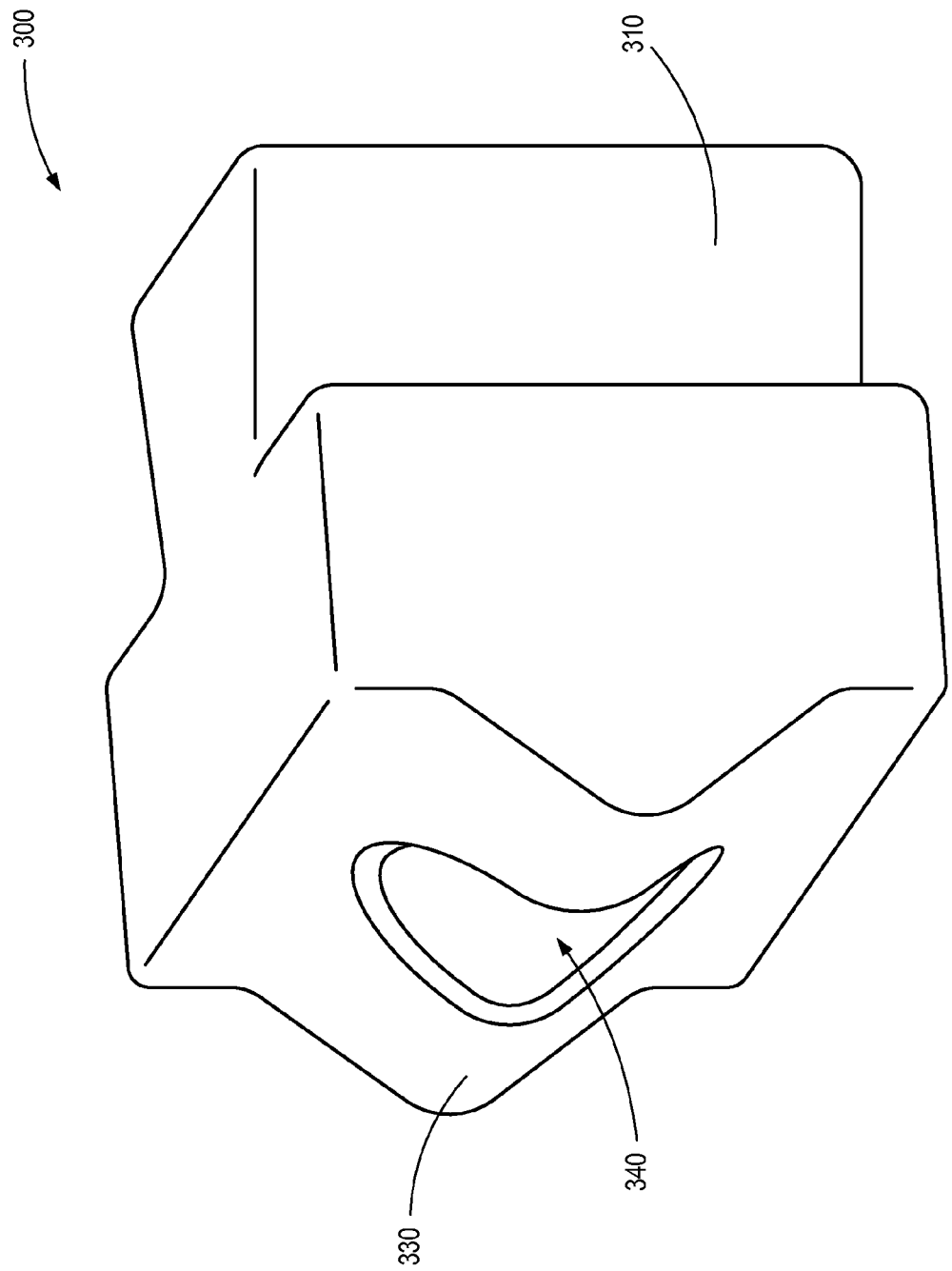
FIG. 24 is a perspective view of the intermediary piece depicted in FIG. 24.

FIG. 23 depicts a side elevation view of an embodiment of intermediary piece 300. As shown in this figure, intermediary piece 300 comprises a protrusion 330. Protrusion 330 is configured to be received in and engage recess 130. As such, preferably protrusion 330 has a shape that is complementary to recess 130 such that they can fit together and maintain maximal surface area contact during engagement and use.

As also shown in this figure, protrusion 330 is defined by two at least substantially flat surfaces 332 and 334 interconnected by a curved surface 335, similar to the way in which recess 130 is defined, as discussed above. As such, when protrusion 330 is engaged with recess 130, surface 332 is configured to engage surface 132, surface 334 is configured to engage surface 134, and curved surface 335 is configured to engage curved surface 135. By matching these surfaces together in this manner, application of forces in a point and/or line manner during engagement, such as during a rotation or "flip" maneuver of implant 100, can be reduced or eliminated.

Surface 334 extends from surface 332 at an angle "B." Preferably, angle B is at least substantially identical to angle A (see FIG. 21) such that protrusion 330 fits within recess 130 and applies maximal surface area contact during surgical procedures, such as the rotation or "flip" maneuver mentioned above. As such, in certain preferred embodiments, angle B—like angle A—may be between about 90 degrees and about 120 degrees. In some such embodiments, angle B may be between about 100 degrees and about 110 degrees.

FIG. 24 depicts a perspective view of intermediary piece 300. This figure illustrates that protrusion 310 is positioned on a side of intermediary piece 300 opposite from protrusion 330. In addition, it can be seen in this figure that protrusion 310 extends along an axis of intermediary piece 300 that is perpendicular to the axis along which protrusion 330 extends. An opening 340 is formed within protrusion 330. As discussed above, opening 340 may extend all the way through intermediary piece 300 (and therefore also through protrusion 310), and may be configured to receive a shaft piece of an inserter, such as inserter 200, which may extend all of the way through opening 340 and into opening 140 formed within rear end wall surface 112 of spinal implant 100.

Figure 25:
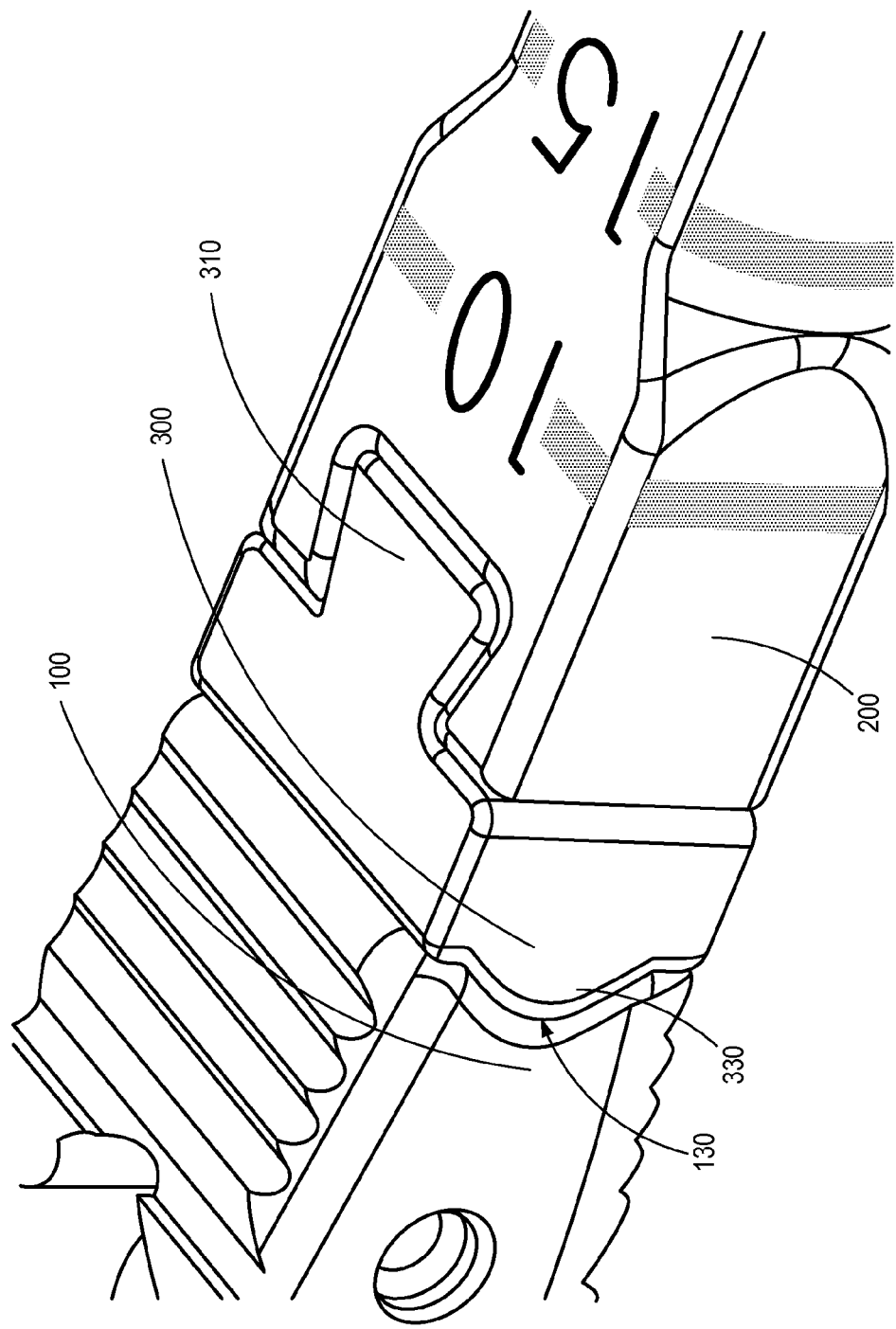
FIG. 25 is a perspective view of embodiments of a spinal implant, an inserter, and an intermediary piece each positioned in engagement with one another.

FIG. 25 depicts a perspective view of an embodiment of spinal implant 100, inserter 200, and intermediary piece 300 each positioned in engagement with one another. As shown in this figure, protrusion 310 is positioned on a first side of intermediary piece 300 and extends into a corresponding recess formed within an end of inserter 200. Similarly, protrusion 330, which is positioned on a second side of intermediary piece 300 opposite from the first side, extends into a recess 130 of spinal implant 100. This interface therefore provides a firm, stable connection that may be less susceptible to resulting in damage and may provide a superior feel to a surgeon/user.

It can also be seen in FIG. 25 that protrusion 330 has a shape that at least substantially matches recess 130 and is configured to allow for coupling with implant 100 by approximating implant 100 and inserter 200 along a common axis of these devices, whereas protrusion 310 has a different shape that expands in diameter as protrusion 310 extends away from the body of intermediary piece 300. In this manner, intermediary piece 300 must be approximated with inserter 200 along an axis that is at least substantially perpendicular to the elongated axis of inserter 200. This coupling also provides for a more secure fit between inserter 200 and intermediary piece 300. In addition, as depicted in FIG. 25, protrusion 310 extends not only along an opposite side of intermediary piece 300 relative to protrusion 330, but also extends along a plane that is at least substantially perpendicular to the plane along which protrusion 330 extends.

It will be understood by those having skill in the art that changes may be made to the details of the above-described embodiments without departing from the underlying principles presented herein. Any suitable combination of various embodiments, or the features thereof, is contemplated. For example, although the depicted embodiments include spinal implants comprising recesses configured to receive protrusions positioned on an inserter, other embodiments are contemplated in which the spinal implant comprises one or more protrusions configured to fit within complementary recess or recesses formed within the inserter.

However, it is thought that, for certain applications and implementations, it may be preferable to form the recess within the spacer, as disclosed in the depicted embodiments, because otherwise the length of the spacer would be increased in the middle (from a top to bottom perspective). This may result confusion among surgeons who are used to viewing such an implant from a top or bottom perspective and assuming such a view defines the dimensions of the inferior and superior surfaces of the implant.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment.

It will be apparent to those having skill in the art that changes may be made to the details of the above-described embodiments without departing from the underlying principles set forth herein. The scope of the present invention should, therefore, be determined only by the following claims.

The invention claimed is:

1. A system for installing a spinal implant, comprising:
   a spinal implant comprising:
      an upper surface;
      a lower surface;
      a first side wall surface;
      a second side wall surface opposite from the first side wall surface;
      a front end wall surface; and
      a rear end wall surface opposite from the front end wall surface, wherein the rear end wall surface comprises at least one of a recess and a protrusion comprising two at least substantially flat surfaces interconnected by a curved surface, wherein the two at least substantially flat surfaces are not parallel and extend relative to one another at a first angle; and
   a tool comprising at least one of a recess and a protrusion configured to fit within the corresponding recess or protrusion of the spinal implant, wherein the at least one of a recess and a protrusion of the tool comprises two at least substantially flat surfaces interconnected by a curved surface, wherein the two at least substantially flat surfaces of the at least one of a recess and a protrusion of the tool are not parallel and extend relative to one another at a second angle, wherein the second angle is at least substantially identical to the first angle, and wherein the at least one of a recess and a protrusion of the tool is further configured such that the curved surface of the at least one of a recess and a protrusion of the tool is configured to at least substantially mate and fit within the at least one of a recess and a protrusion of the spinal implant such that the curved surface of the at least one of a recess and a protrusion of the tool contacts the curved surface of the at least one of a recess and a protrusion of the spinal implant.

2. The system of claim 1, wherein the rear end wall surface further comprises an opening configured to facilitate engagement with the tool.

3. The system of claim 1, wherein the first angle is at least about 90 degrees.

4. The system of claim 3, wherein the first angle is between about 90 degrees and about 120 degrees.

5. The system of claim 4, wherein the first angle is between about 100 degrees and about 110 degrees.

6. The system of claim 1, wherein the tool comprises an inserter tool, and wherein the at least one of a recess and a protrusion of the tool is positioned at a distal end of the inserter tool.

7. The system of claim 1, further comprising an inserter tool, wherein the tool comprises an intermediary piece configured to be coupled with the spinal implant and the inserter tool in between the spinal implant and the inserter tool.

8. The system of claim 7, wherein the intermediary piece comprises a central opening extending all of the way through the intermediary piece, and wherein the central opening is configured to receive a shaft of the inserter tool.

9. The system of claim 7, wherein the intermediary piece comprises:
   a first protrusion extending from a first end of the intermediary piece, wherein the first protrusion is configured to be received within a corresponding recess formed within the spinal implant; and
   a second protrusion extending from a second end of the intermediary piece opposite from the first end, wherein the second protrusion is configured to be received within a corresponding recess formed within the inserter tool.

10. The system of claim 9, wherein the second protrusion extends along a plane that is at least substantially perpendicular to a plane along which the first protrusion extends.

11. The system of claim 9, wherein the second protrusion expands in diameter as the second protrusion extends away from a body of the intermediary piece.

12. The system of claim 1, wherein the at least one of a recess and a protrusion of the spinal implant and the at least one of a recess and a protrusion of the tool are configured such that the interface between the at least one of a recess and a protrusion of the spinal implant and the at least one of a recess and a protrusion of the tool at least substantially eliminates any point or line contacts between the tool and the spinal implant during a flip maneuver of the spinal implant within an intervertebral space of a patient.

13. The system of claim 12, wherein the spinal implant comprises a silicon nitride ceramic material.

14. The system of claim 1, wherein the first angle is between about 5 degrees and about 175 degrees or between about 185 degrees and about 355 degrees.

15. A system for installing a spinal implant, comprising:
   a spinal implant comprising:
      an upper surface;
      a lower surface;
      a first side wall surface;
      a second side wall surface opposite from the first side wall surface;
      a front end wall surface; and
      a rear end wall surface opposite from the front end wall surface, wherein the rear end wall surface comprises a recess comprising two at least substantially flat surfaces interconnected by a curved surface, wherein the two at least substantially flat surfaces are not parallel and extend relative to one another at a first angle, wherein the first angle is between about 100 degrees and about 110 degrees, and wherein the rear end wall surface further comprises an opening formed within the recess and configured to facilitate engagement with an inserter tool; and
   an inserter tool comprising a protrusion configured to fit within the recess of the spinal implant, wherein the protrusion comprises two at least substantially flat surfaces interconnected by a curved surface, wherein the two at least substantially flat surfaces of the protrusion are not parallel and extend relative to one another at a second angle, wherein the second angle is at least substantially identical to the first angle, wherein the protrusion is further configured such that the curved surface of the protrusion is configured to at least substantially mate and fit within the recess the spinal implant so as to at least substantially eliminate any point or line contacts between the inserter tool and the spinal implant during a flip maneuver of the spinal implant within an intervertebral space of a patient using the inserter tool and such that the curved surface of the protrusion of the tool contacts the curved surface of the recess of the spinal implant.

16. The system of claim 15, wherein the inserter tool further comprises an intermediary piece, and wherein the protrusion is formed at a distal end of the intermediary piece.

* * * * *

UNITED STATES PATENT AND TRADEMARK OFFICE
CERTIFICATE OF CORRECTION

PATENT NO. : 9,668,882 B2
APPLICATION NO. : 14/175902
DATED : June 6, 2017
INVENTOR(S) : Prabhakar Thirugnanasambandam et al.

It is certified that error appears in the above-identified patent and that said Letters Patent is hereby corrected as shown below:

On the Title Page

- (63) Related Application Data delete ", and application No. 14/175,902, Feb. 7, 2014"

Signed and Sealed this
Ninth Day of January, 2018

Joseph Matal
*Performing the Functions and Duties of the*
*Under Secretary of Commerce for Intellectual Property and*
*Director of the United States Patent and Trademark Office*